US009133162B2

(12) United States Patent
Xi

(10) Patent No.: US 9,133,162 B2
(45) Date of Patent: Sep. 15, 2015

(54) SUBSTITUTED QUINOLINE COMPOUNDS AND METHODS OF USE

(75) Inventor: Ning Xi, Newbury Park, CA (US)

(73) Assignees: SUNSHINE LAKE PHARMA CO., LTD., Dongguan, Guangdong (CN); CALITOR SCIENCES, LLC, Newbury Park, CA (US)

( * ) Notice: Subject to any disclaimer, the term of this patent is extended or adjusted under 35 U.S.C. 154(b) by 121 days.

(21) Appl. No.: 13/400,586

(22) Filed: Feb. 21, 2012

(65) Prior Publication Data

US 2012/0219522 A1 Aug. 30, 2012

Related U.S. Application Data

(60) Provisional application No. 61/447,104, filed on Feb. 28, 2011.

(51) Int. Cl.
*A61K 31/4709* (2006.01)
*C07D 401/12* (2006.01)
*A61K 38/21* (2006.01)
*A61K 45/06* (2006.01)
*A61K 31/436* (2006.01)

(52) U.S. Cl.
CPC ............ *C07D 401/12* (2013.01); *A61K 31/436* (2013.01); *A61K 31/4709* (2013.01); *A61K 38/21* (2013.01); *A61K 45/06* (2013.01)

(58) Field of Classification Search
CPC ......................... C07D 401/12; A61K 31/4709
USPC ............................ 546/153; 514/280, 312, 314
See application file for complete search history.

(56) References Cited

U.S. PATENT DOCUMENTS

| | | | |
|---|---|---|---|
| 7,723,330 B2 | 5/2010 | Blake et al. | |
| 7,732,613 B2 | 6/2010 | Kim | |
| 7,759,344 B2 | 7/2010 | Booker et al. | |
| 7,858,623 B2 | 12/2010 | Kim et al. | |
| 7,880,004 B2 | 2/2011 | Borzilleri et al. | |
| 8,030,302 B2 | 10/2011 | Li et al. | |
| 8,088,794 B2 | 1/2012 | Kim et al. | |
| 8,093,264 B2 | 1/2012 | Saavedra et al. | |
| RE43,878 E | 12/2012 | Li et al. | |
| 8,445,509 B2 | 5/2013 | Miyamoto et al. | |
| 8,569,295 B2 | 10/2013 | Chen et al. | |
| 2008/0004273 A1 | 1/2008 | Raeppel et al. | |
| 2008/0312232 A1* | 12/2008 | Kim et al. | 514/235.2 |
| 2009/0087431 A1 | 4/2009 | Yaworsky et al. | |
| 2009/0306103 A1 | 12/2009 | Boyer et al. | |
| 2010/0093727 A1 | 4/2010 | Xi | |
| 2010/0239576 A1 | 9/2010 | Xi | |
| 2010/0256356 A1 | 10/2010 | Blake et al. | |
| 2011/0046169 A1 | 2/2011 | Miyamoto et al. | |
| 2011/0053906 A1 | 3/2011 | Huck et al. | |
| 2011/0053931 A1 | 3/2011 | Gaudino et al. | |
| 2011/0104161 A1 | 5/2011 | Burgess et al. | |
| 2011/0183983 A1 | 7/2011 | Kim et al. | |
| 2011/0229469 A1 | 9/2011 | Johns | |
| 2012/0070413 A1 | 3/2012 | Kim et al. | |
| 2012/0289509 A1 | 11/2012 | Kim et al. | |
| 2013/0123286 A1 | 5/2013 | Hu et al. | |
| 2013/0225569 A1 | 8/2013 | Burgdorf et al. | |

FOREIGN PATENT DOCUMENTS

| | | |
|---|---|---|
| CN | 102086211 A | 6/2011 |
| CN | 102212062 A | 10/2011 |
| CN | 103420986 A | 12/2013 |
| WO | 2009096435 A | 8/2009 |
| WO | WO 2009096435 | 8/2009 |
| WO | WO 2011017142 | 2/2011 |
| WO | 2012008564 A | 1/2012 |
| WO | WO 2012006960 | 1/2012 |
| WO | WO 2012008564 | 1/2012 |
| WO | 2012028332 A | 3/2012 |
| WO | WO 2012025187 | 3/2012 |
| WO | WO 2012028332 | 3/2012 |
| WO | 2012044577 A | 4/2012 |
| WO | 2013180949 A | 12/2013 |

OTHER PUBLICATIONS

Liu et al., Structure-Based Design of Novel Class II c-Met Inhibitors: 2. SAR and Kinase Selectivity Profiles of the Pyrazolone Series, J. Med. Chem., 2012, vol. 55, Issue 5, p. 1868-1897.
Norman et al., Structure-Based Design of Novel Class II c-Met Inhibitors: 1. Identification of Pyrazolone-Based Derivatives, J. Med. Chem., 2012, vol. 55, Issue 5, p. 1858-1867.
Allen et al., The discovery of benzanilides as c-Met receptor tyrosine kinase inhibitors by a directed screening approach, Bioorg. Med. Chem. Lett., 2011, vol. 21, Issue 18, p. 5224-5229.
Teffera et al., Chemical Reactivity of Methoxy 4-O-Aryl Quinolines: Identification of Glutathione Displacement Products in Vitro and in Vivo, Chem. Res. Toxicol., 2008, vol. 21, Issue 11, p. 2216-2222.
Zhang et al., Identification of a Novel Recepteur d'Origine Nantais/c-Met Small-Molecule Kinase Inhibitor with Antitumor Activity In vivo, Cancer Res. 2008, vol. 68, Issue 16, p. 6680-6687.
Liu et al., Discovery of a Potent, Selective, and Orally Bioavailable c-Met Inhibitor: 1-(2-Hydroxy-2-methylpropyl)-N-(5-(7-methoxyquinolin-4-yloxy)pyridin-2-yl)-5-methyl-3-oxo-2-phenyl-2,3-dihydro-1H-pyrazole-4-carboxamide (AMG 458), J. Med. Chem., 2008, vol. 51, Issue 13, p. 3688-3691.
Liu et al., J. Med. Chem., Jun. 14, 2008, vol. 51, No. 13, p. 3688-3691.
Liu, Longbin; Norman, Mark H.; Lee, Matthew; Xi, Ning; et al., J. Med. Chem., Feb. 9, 2012, vol. 55, No. 5, p. 1868-1897.
Norman, Mark H.; Liu, Longbin; Lee, Matthew; Xi, Ning;et al., J. Med. Chem., Feb. 9, 2012, vol. 55, No. 5, p. 1858-1867.
Teffera, Yohannes; Colletti, Adria E.; Harmange, Jean Christophe;et al., Chem. Res. Toxicol., Oct. 7, 2008, vol. 21, No. 11, p. 2216-2222.
Zhang, Yihong; Kaplan-Lefko, Paula J.; Rex, Karen;Yang, Yajing; et al., Cancer Res., Aug. 15, 2008, vol. 68, No. 16, p. 6680-6687.

* cited by examiner

*Primary Examiner* — Jeffrey S Lundgren
*Assistant Examiner* — Sarah E Townsley
(74) *Attorney, Agent, or Firm* — Kam. W. Law; Squire Patton Boggs

(57) ABSTRACT

The present invention provides novel substituted quinoline compounds, pharmaceutical acceptable salts and formulations thereof useful in modulating the protein tyrosine kinase activity, and in modulating cellular activities such as proliferation, differentiation, apoptosis, migration and invasion. The invention also provides pharmaceutically acceptable compositions comprising such compounds and methods of using the compositions in the treatment of hyperproliferative disorders in mammals, especially humans.

8 Claims, 3 Drawing Sheets

SUBSTITUTED QUINOLINE COMPOUNDS AND METHODS OF USE

CROSS-REFERENCE TO RELATED APPLICATIONS

This application claims the benefit of U.S. provisional application No. 61/447,104, filed Feb. 28, 2011, the content of which is hereby incorporated by reference in its entirety.

FIELD OF THE INVENTION

This invention relates to novel substituted quinoline compounds, and salts thereof, which are useful in the treatment of hyperproliferative diseases, such as cancers, in mammals. In particular, the invention relates to compounds that inhibit the protein tyrosine kinase activity, resulting in the inhibition of inter- and/or intra-cellular signaling. This invention also relates to a method of using such compounds in the treatment of hyperproliferative diseases in mammals, especially humans, and to pharmaceutical compositions containing such compounds.

BACKGROUND OF THE INVENTION

Protein kinases represent a large family of proteins that play a central role in the regulation of a wide variety of cellular processes. Through regulating an array of signaling pathways, protein kinases control cell metabolism, cell cycle progression, cell proliferation and cell death, differentiation and survival. There are over 500 kinases in the human kinome, and over 150 of these have been shown or are proposed to be involved in the onset and/or progression of various human diseases including inflammatory diseases, cardiovascular diseases, metabolic diseases, neurodegenerative diseases and cancer.

A partial list of such kinases include abl, AATK, ALK, Akt, Axl, bmx, bcr-abl, Blk, Brk, Btk, csk, c-kit, c-Met, c-src, c-fms, CDK1, CDK2, CDK3, CDK4, CDK5, CDK6, CDK7, CDK8, CDK9, CDK10, cRaf1, CSF1R, CSK, DDR1, DDR2, EPHA, EPHB, EGFR, ErbB2, ErbB3, ErbB4, Erk, Fak, fes, FER, FGFR1, FGFR2, FGFR3, FGFR4, FGFR5, Fgr, flt-1, Fps, Frk, Fyn, GSG2, GSK, Hck, ILK, INSRR, IRAK4, ITK, IGF-1R, INS-R, Jak, KSR1, KDR, LMTK2, LMTK3, LTK, Lck, Lyn, MATK, MERTK, MLTK, MST1R, MUSK, NPR1, NTRK, MEK, MER, PLK4, PTK, p38, PDGFR, PIK, PKC, PYK2, RET, ROR1, ROR2, RYK, ros, Ron, SGK493, SRC, SRMS, STYK1, SYK, TEC, TEK, TEX14, TNK1, TNK2, TNNI3K, TXK, TYK2, Tyro-3, tie, tie2, TRK, Yes, and Zap70.

Protein tyrosine kinases are a subclass of protein kinase. They also may be classified as growth factor receptor (e.g. Axl, VEGFR, c-Met (HGFR), EGFR, PDGFR, and FGFR) or non-receptor (e.g. c-src and bcr-abl) kinases. Receptor tyrosine kinases are transmembrane proteins that possess an extracellular binding domain for growth factors, a transmembrane domain, and an intracellular portion that functions as a kinase to phosphorylate a specific tyrosine residue in proteins. Abnormal expression or activity of protein kinases has been directly implicated in the pathogenesis of myriad human cancers.

Angiogenesis, the formation of new capillaries from pre-existing blood vessels, is a necessary process for organ development during embryogenesis and is critical for the female reproductive cycle, inflammation, and wound healing in the adult. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Solid tumors, in particular, are dependent on angiogenesis to grow beyond a certain critical size by inducing new capillaries sprouting from existing blood vessels to secure their nutrition, oxygen supply, and waste removal. In addition, angiogenesis also promotes metastasis of tumor cells to other sites.

The new vessel growth and maturation are highly complex and coordinated processes, requiring the stimulation by a number of growth factors, but vascular endothelial growth factor (VEGF) signaling often represents a critical rate-limiting step in physiological angiogenesis and pathological angiogenesis. VEGF binds to and activates the receptor tyrosine kinase, VEGFR. Three VEGFR isoforms have been identified in humans: VEGFR-1 (Flt-1), VEGFR-2 (KDR/Flk-1) and VEGFR-3 (Flt-4). VEGFR-2 mediates the majority of cellular responses to VEGF, in particular its mitogenic and angiogenic effects. VEGFR-1 is thought to modulate VEGFR-2 signaling or to act as a dummy/decoy receptor to sequester VEGF away from VEGFR-2. The expression of VEGFR-1 is also up-regulated by hypoxia, in a similar mechanism to VEGF, via HIF-1; its functions may vary depending on cell type and developmental stage. (Stuttfeld E, Ballmer-Hofer K (September 2009). "Structure and function of VEGF receptors". *IUBMB Life* 61 (9): 915-22.)

Since VEGFR-2 is the major mediator of vascular endothelial cell (EC) mitogenesis and survival, as well as angiogenesis and microvascular permeability, it is expected that direct inhibition of the kinase activity of VEGFR-2 will result in the reduction of angiogenesis and the suppression of tumor growth. Furthermore, inhibition of VEGFR-2 targeting the genetically more stable host endothelial cells, instead of labile tumor tissues, may decrease the chance of resistance development. Several agents targeting VEGFR signaling, administered either as single agents or in combination with chemotherapy, have been shown to benefit patients with advanced-stage malignancies. ("VEGF-targeted therapy: mechanisms of anti-tumor activity." *Nature Reviews Cancer,* 2008, 8, 579; "Molecular basis for sunitinib efficacy and future clinical development." *Nature Reviews Drug Discovery,* 2007, 6, 734; "Angiogenesis: an organizing principle for drug discovery?" *Nature Reviews Drug Discovery,* 2007, 6, 273).

c-Met, also referred to as hepatocyte growth factor receptor (HGFR), is expressed predominantly in epithelial cells but has also been identified in endothelial cells, myoblasts, hematopoietic cells and motor neurons. The natural ligand for c-Met is hepatocyte growth factor (HGF), also known as scatter factor (SF). In both embryos and adults, activated c-Met promotes a morphogenetic program, known as invasive growth, which induces cell spreading, the disruption of inter-cellular contacts, and the migration of cells towards their surroundings. ("From Tpr-Met to Met, tumorigenesis and tubes." Oncogene 2007, 26, 1276; "Met Receptor Tyrosine Kinase as a Therapeutic Anticancer Target." Cancer Letter, 2009, 280, 1-14).

A wide variety of human malignancies exhibit sustained c-Met stimulation, overexpression, or mutation, including carcinomas of the breast, liver, lung, ovary, kidney, thyroid, colon, renal, glioblastomas, and prostate, etc. c-Met is also implicated in atherosclerosis and lung fibrosis. Invasive growth of certain cancer cells is drastically enhanced by tumor-stromal interactions involving the HGF/c-Met pathway. Thus, extensive evidence that c-Met signaling is involved in the progression and spread of several cancers and an enhanced understanding of its role in disease have generated considerable interest in c-Met as major targets in cancer drug development. ("Molecular cancer therapy: can our expectation be MET." Euro. J. Cancer, 2008, 44, 641-651; "Targeting the c-Met Signaling Pathway in Cancer." Clin. Cancer Res. 2006, 12, 3657). Agents targeting c-Met signaling pathway are now under clinical investigation. ("Novel Therapeutic Inhibitors of the c-Met Signaling Pathway in Cancer." Clinical Cancer Research, 2009, 15, 2207). "Drug development of MET inhibitors: targeting oncogene addiction and expedience." *Nature Review Drug Discovery,* 2008, 7, 504).

Axl belongs to the subfamily of receptor tyrosine kinases (RTKs) that also includes Tyro3 and Mer (TAM). The TAM receptors are characterized by a combination of two immunoglobin-like domains and dual fibronectin type III repeats in the extracellular region and a cytoplasmic kinase domain. The ligands for TAM receptors are Gas6 (growth arrest-specific 6) and protein S, two vitamin K-dependent proteins that exhibit 43% amino-acid sequence identity and share similar domain structures ("The anticoagulation factor protein S and its relative, Gas6, are ligands for the Tyro 3/Axl family of receptor tyrosine kinases." Cell, 1995, 80, 661-670; "Axl receptor tyrosine kinase stimulated by the vitamin K-dependent protein encoded by growth-arrest-specific gene 6." Nature, 1995, 373, 623-626).

Adequate evidence supports the role of the Gas6/Axl system in driving cell growth and survival in normal and cancer cells (TAM receptor tyrosine kinases: biologic functions, signaling, and potential therapeutic targeting in human cancer. Adv Cancer Res 2008, 100, 35-83). Axl overexpression and signaling has been implicated in several human malignancies, such as colon, breast, glioma, thyroid, gastric, melanoma, lung cancer, and in renal cell carcinoma (RCC). A more detailed role of Axl biology has been proven in glioma, where loss of Axl signaling diminished glioma tumor growth, and in breast cancer, where Axl drive cell migration, tube formation, neovascularization, and tumor growth. Axl has been shown to play multiple roles in tumorigenesis and that therapeutic antibodies against Axl may block Axl functions not only in malignant tumor cells but also in the tumor stroma. The additive effect of Axl inhibition with anti-VEGF suggests that blocking Axl function could be an effective approach for enhancing antiangiogenic therapy. ("Axl as a potential therapeutic target in cancer: role of Axl in tumor growth, metastasis and angiogenesis." Oncogene, 2009, 28, 3442-3455; "TAM Receptor Tyrosine Kinases: Biologic Functions, Signaling, and Potential Therapeutic Targeting in Human Cancer." Adv Cancer Res. 2008, 100, 35-83).

It is widely known that cancer cells employ multiple mechanisms to evade tightly regulated cellular processes such as proliferation, apoptosis, and senescence. Thus, most tumors can escape from the inhibition of any single kinase. System-wide analyses of tumors identified receptor tyrosine kinase (RTK) coactivation as an important mechanism by which cancer cells achieve chemoresistance. One of the strategies to overcome RTK coactivation may involve therapeutically targeting multiple RTKs simultaneously in order to shut down oncogenic RTK signaling and overcome compensatory mechanisms. ("Receptor Tyrosine Kinas Coactivation Networks in Cancer." Cancer Research, 2010, 70, 3857). Anti-tumor approaches in targeting VEGFR, c-Met and Axl signaling may circumvent the ability of tumor cells to overcome VEGFR, c-Met (HGFR) and/or Axl inhibition alone and thus may represent improved cancer therapeutics.

SUMMARY OF THE INVENTION

The present invention provides new compounds and methods for treating cell proliferative diseases. The compounds of the invention are inhibitors of protein tyrosine kinases. Preferably, the compounds of the invention are multiple function inhibitors, capable of inhibiting, for example, VEGFR, c-Met (HGFR) and Axl receptor signaling. Accordingly, the invention provides new inhibitors of protein tyrosine kinase receptor signaling, such as for example, VEGF receptor signaling, HGF receptor signaling, and Axl receptor signaling.

Specifically, it has been found that compounds of this invention, and pharmaceutically acceptable compositions thereof, are effective as inhibitors of receptor tyrosine kinases such as VEGFR, c-Met, and Axl. Accordingly, the invention provides compounds having the formula I:

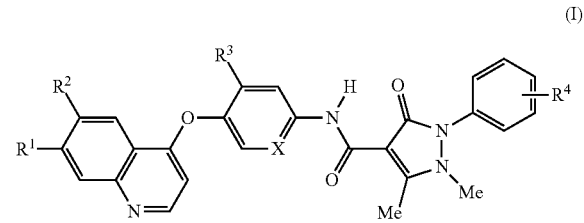

and stereoisomers, geometric isomers, tautomers, solvates, metabolites, and salts thereof, wherein each of $R^1$, $R^2$, $R^3$, $R^4$, X is as defined herein.

One aspect of the invention provides compositions comprising a compound that is an inhibitor of receptor tyrosine kinase, or a stereoisomer, geometric isomer, tautomer, solvate, metabolite, pharmaceutically acceptable salt thereof, and a pharmaceutically acceptable carrier, excipient or diluent. In some embodiments, the invention provides compositions comprising a compound that is an inhibitor of VEGF receptor signaling, HGF receptor signaling and Axl receptor signaling, or a stereoisomer, geometric isomer, tautomer, solvate, metabolite, pharmaceutically acceptable salt thereof, and a pharmaceutically acceptable carrier, excipient, or diluent. In other embodiments, the composition further comprises an additional therapeutic agent.

Another aspect of the invention provides a method of inhibiting protein tyrosine kinase, the method comprising contacting the kinase with a compound according to the present invention, or with a composition according to the present invention. In some embodiments, the invention provides a method of inhibiting VEGF receptor signaling, HGF receptor signaling and Axl receptor signaling, the method comprising contacting the receptor with a compound according to the present invention, or with a composition according to the present invention Inhibition of receptor protein kinase activity, preferably VEGF, HGF and Axl receptor signaling, can be in a cell or a multicellular organism. If in a multicellular organism, the method according to this aspect of the invention comprises administering to the organism a compound according to the present invention, or a composition according to the present invention. In some embodiments, the organism is a mammal. In other embodiments is a human. In yet another embodiment, the method further comprises contacting the kinase with an additional therapeutic agent.

Another aspect of the invention provides a method of inhibiting proliferative activity of a cell, the method comprising contacting the cell with an effective proliferative inhibiting amount of a compound according to the present invention or a composition thereof. In some embodiments, the method further comprises contacting the cell with an additional therapeutic agent.

Another aspect of the invention provides a method of treating a cell proliferative disease in a patient, the method comprising administering to the patient in need of such treatment an effective therapeutic amount of a compound according to the present invention or a composition thereof. In some embodiments, the method further comprises administering an additional therapeutic agent.

Another aspect of the invention provides a method of inhibiting tumor growth in a patient, the method comprising administering to the patient in need thereof an effective therapeutic amount of a compound according to the present invention or a composition thereof. In some embodiments, the method further comprises administering an additional therapeutic agent.

Another aspect of the invention includes methods of preparing, methods of separating, and methods of purifying compounds of Formula (I).

The foregoing merely summarizes certain aspects of the invention and is not intended to be limiting in nature. These aspects and other aspects and embodiments are described more fully below.

DETAILED DESCRIPTION OF THE INVENTION

Definitions and General Terminology

Figure 1:
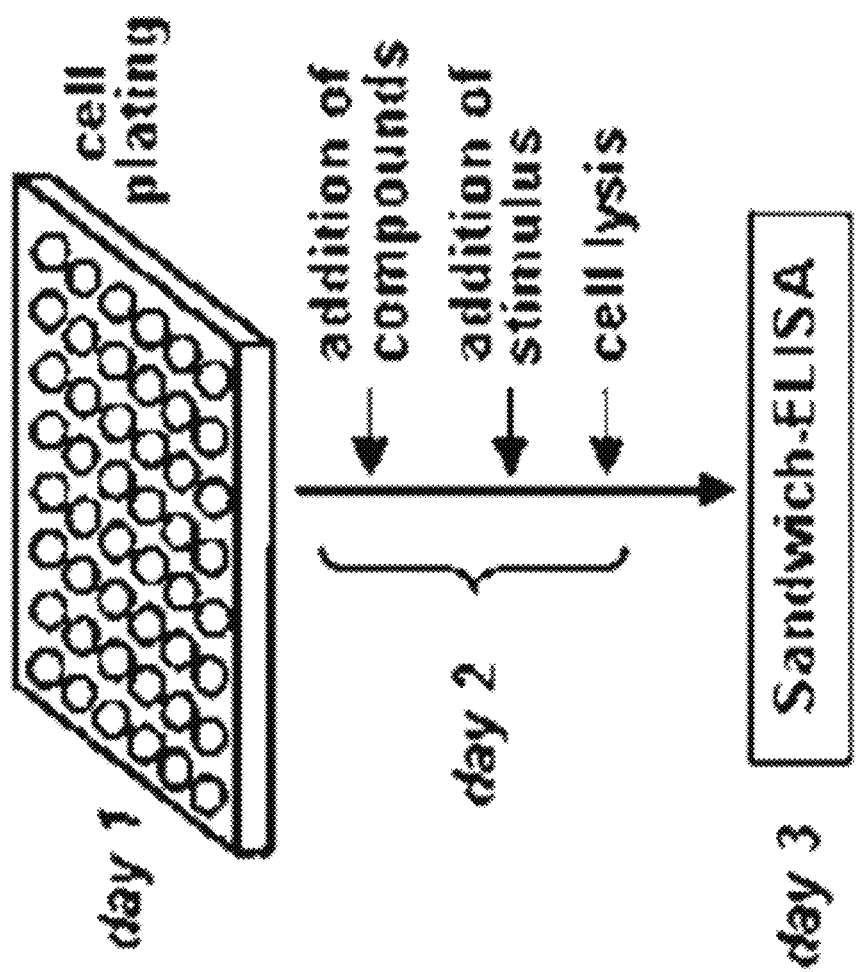
FIG. 1 depicts the steps of the cellular phosphorylation assay.

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," by Michael B. Smith and Jerry March, John Wiley & Sons, New York: 2007, the entire contents of which are hereby incorporated by reference.

As described herein, compounds of the invention may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". In general, the term "substituted" whether proceeded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

The term "alkyl" or "alkyl group" as used herein refers to a saturated linear or branched-chain monovalent hydrocarbon radical of one to twenty carbon atoms, wherein the alkyl radical may be optionally substituted independently with one or more substituents described below. Unless otherwise specified, alkyl groups contain 1-20 carbon atoms. In some embodiments, alkyl groups contain 1-10 carbon atoms. In other embodiments, alkyl groups contain 1-8 carbon atoms. In still other embodiments, alkyl groups contain 1-6 carbon atoms, and in yet other embodiments, alkyl groups contain 1-4 carbon atoms.

Examples of alkyl groups include, but are not limited to, methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (1-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$), 1-heptyl, 1-octyl, and the like.

The terms "alkyl" and the prefix "alk-" as used herein, are inclusive of both straight chain and branched saturated carbon chain.

The term "alkoxy" as used herein, refers to an alkyl group, as previously defined, attached to the principal carbon atom through an oxygen atom. Unless otherwise specified, alkoxy groups contain 1-20 carbon atoms. In some embodiments, alkoxy groups contain 1-10 carbon atoms. In other embodiments, alkoxy groups contain 1-8 carbon atoms. In still other embodiments, alkoxy groups contain 1-6 carbon atoms, and in yet other embodiments, alkoxy groups contain 1-4 carbon atoms.

Examples of alkoxy groups include, but are not limited to, methoxy (MeO, $-OCH_3$), ethoxy (EtO, $-OCH_2CH_3$), 1-propoxy (n-PrO, n-propoxy, $-OCH_2CH_2CH_3$), 2-propoxy (i-PrO, i-propoxy, $-OCH(CH_3)_2$), 1-butoxy (n-BuO, n-butoxy, $-OCH_2CH_2CH_2CH_3$), 2-methyl-1-propoxy (s-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like.

The term "hydroxyalkoxy" embraces liner or branched alkoxy radicals substituted with one or more hydroxyl radicals. Unless otherwise specified, hydroxyalkoxy groups contain 1-20 carbon atoms. In some embodiments, hydroxyalkoxy groups contain 1-10 carbon atoms. In other embodiments, hydroxyalkoxy groups contain 1-8 carbon atoms. In still other embodiments, hydroxyalkoxy groups contain 1-6 carbon atoms, and in yet other embodiments, hydroxyalkoxy groups contain 1-4 carbon atoms. In some embodiments, hydroxyalkoxy groups contain 1-4 hydroxyl groups. In other embodiments, hydroxyalkoxy groups contain 1-3 hydroxyl groups. In still other embodiments, hydroxyalkoxy groups contain 1-2 hydroxyl groups, and in yet other embodiments, hydroxyalkoxy groups contain one hydroxyl group.

Examples of hydroxyalkoxy groups include, but are not limited to, hydroxyethoxy (—OCH$_2$CH$_2$OH), 2-hydroxypropoxy (—OCH$_2$CH(OH)CH$_3$), 3-hydroxypropoxy (—OCH$_2$CH$_2$CH$_2$OH), —OCH$_2$CH(OH)CH$_2$OH, —OCH(CH$_3$)(CH$_2$OH), —OCH$_2$CH(OH)CH$_2$CH$_3$, —OCH$_2$CH$_2$CH(OH)CH$_3$, —OCH$_2$CH$_2$CH$_2$CH$_2$OH, —OCH$_2$C(OH)(CH$_3$)$_2$, —OCH$_2$CH(CH$_2$OH)$_2$, —OCH$_2$CH(CH$_3$)(CH$_2$OH), —OCH$_2$C(OH)(CH$_3$)(CH$_2$OH), —OCH(CH$_3$)CH(OH)CH$_3$, —OCH(CH$_2$OH)CH$_2$CH$_3$, —OC(CH$_3$)$_2$(CH$_2$OH), —OC(CH$_3$)(CH$_2$OH)$_2$, and the like.

The terms "haloalkyl" and "haloalkoxy" means alkyl, or alkoxy, as the case may be, substituted with one or more halogen atoms.

The term "carbocycle", "carbocyclyl", "carbocyclic ring" and "cycloaliphatic" refers to a monovalent or multivalent non-aromatic, saturated or partially unsaturated ring having 3 to 12 carbon atoms as a monocyclic, bicyclic, or tricyclic ring system. Suitable cycloaliphatic groups include, but are not limited to, cycloalkyl, cycloalkenyl, and cycloalkynyl. Further examples of cycloaliphatic groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, and the like.

The term "heterocycle," "heterocyclyl," or "heterocyclic" as used interchangeably herein refers to a monocyclic, bicyclic, or tricyclic ring system in which one or more ring members are an independently selected heteroatom and that is completely saturated or that contains one or more units of unsaturation, but which is not aromatic, that has a single point of attachment to the rest of the molecule. One or more ring atoms are optionally substituted independently with one or more substituents described herein. In some embodiments, the "heterocycle", "heterocyclyl", or "heterocyclic" group is a monocycle having 3 to 7 ring members (2 to 6 carbon atoms and 1 to 3 heteroatoms selected from N, O, P, and S, wherein the S or P is optionally substituted with one or more oxo to provide the group SO or SO$_2$, PO or PO$_2$ or a bicycle having 7 to 10 ring members (4 to 9 carbon atoms and 1 to 3 heteroatoms selected from N, O, P, and S, wherein the S or P is optionally substituted with one or more oxo to provide the group SO or SO$_2$, PO or PO$_2$.

The heterocyclyl may be a carbon radical or heteroatom radical. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homo-piperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 1,2,3,4-tetrahydroiso-quinolinyl. Examples of a heterocyclic group wherein 2 ring carbon atoms are substituted with oxo (═O) moieties are pyrimidindionyl and 1,1-dioxo-thiomorpholinyl. The heterocycle groups herein are optionally substituted independently with one or more substituents described herein.

The term "heteroatom" means one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" means F, Cl, Br, or I.

The term "H" denotes a single hydrogen atom. This radical may be attached, for example, to an oxygen atom to form a hydroxyl radical.

The term "aryl" used alone or as part of a larger moiety as in "aralkyl", "aralkoxy" or "aryloxyalkyl" refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring." Examples of aryl rings would include phenyl, naphthyl, and anthracene.

The term "heteroaryl" used alone or as part of a larger moiety as in "heteroaralkyl" or "heteroarylalkoxy" refers to monocyclic, bicyclic, and tricyclic ring systems having a total of five to fourteen ring members, wherein at least one ring in the system is aromatic, at least one ring in the system contains one or more heteroatoms, wherein each ring in the system contains 5 to 7 ring members and that has a single point of attachment to the rest of the molecule. The term "heteroaryl" may be used interchangeably with the term "heteroaryl ring" or the term "heteroaromatic".

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Suitable alkylamino radicals may be mono or dialkylamino such as N-methylamino, N-ethylamino, N,N-dimethylamino, N,N-diethylamino and the like.

The term "arylamino" denotes amino groups, which have been substituted with one or two aryl radicals, such as N-phenylamino. The arylamino radicals may be further substituted on the aryl ring portion of the radical.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl.

The term "unsaturated" as used herein, means that a moiety has one or more units of unsaturation.

The term "comprising" is meant to be open ended, including the indicated component but not excluding other elements.

As described herein, a bond drawn from a substituent to the center of one ring within a ring system (as shown below) represents substitution of the substituent at any substitutable position on the rings to which it is attached. For example, Figure a represents possible substitution in any of the positions on the B ring shown in Figure b.

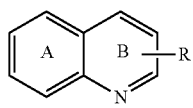

Figure a

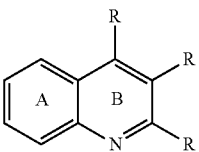

Figure b

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms.

The term "prodrug" as used herein, represents a compound that is transformed in vivo into a compound of formula I. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphonation of an OH group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al, Prodrugs: Design and Clinical Applications, Nature Review Drug Discovery, 2008, 7, 255-270, and S. J. Hecker et al, Prodrugs of Phosphates and Phosphonates, Journal of Medicinal Chemistry, 2008, 51, 2328-2345, each of which is incorporated herein by reference.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture"

and "racemate" refer to an equimolar mixture of two enantiomeric species, devoid of optical activity.

A "pharmaceutically acceptable salt" as used herein, refers to organic or inorganic salts of a compound of the invention. Pharmaceutically acceptable salts are well known in the art. For example, S. M. Berge et al., describe pharmaceutically acceptable salts in detail in J. Pharmaceutical Sciences, 66: 1-19, 1977, which is incorporated herein by reference. Examples of pharmaceutically acceptable, nontoxic salts include, but are not limited to, salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, C$_{1-8}$ sulfonate and aryl sulfonate.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "PG" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl)ethoxy-methyl-1,2-(p-toluenesulfonyl) ethyl, 2-(p-nitrophenylsulfenyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

Description of Compounds of the Invention

The present invention provides quinoline compounds, salts, and pharmaceutical formulations thereof, which are potentially useful in the treatment of diseases, conditions and disorders modulated by receptor tyrosine kinases, especially VEGFR, c-Met and Axl receptor. More specifically, the present invention provides compounds of Formula I:

(I)

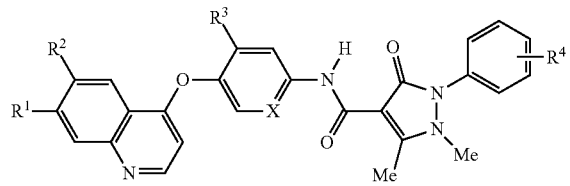

and stereoisomers, geometric isomers, tautomers, solvates, metabolites, and salts thereof, wherein each of R1, R2, R3, R4 and X is as defined herein.

In some embodiments of the compound of Formula (I), each of R$^1$ and R$^2$ is independently H, alkoxy, or hydroxyalkoxy; R$^3$ is H or F; R$^4$ is H, F, Cl, Br, I, CN, alkyl, haloalkyl, heterocyclyl, heterocyclylalkyl, cycloalkyl, or cycloalkylalkyl; and X is CH or N;

In another embodiment, R$^1$ is hydroxy C$_{2-6}$ alkoxy; R$^2$ is H or methoxy; R$^3$ is H or F; R$^4$ is H, F, Cl, Br, I, CN, C$_{1-3}$ haloalkyl, C$_{2-5}$ heterocyclyl, C$_{2-5}$ heterocyclyl C$_{1-3}$ alkyl, C$_{3-6}$ cycloalkyl, C$_{3-6}$ cycloalkyl C$_{1-3}$ alkyl; and X is CH or N.

In another embodiment, R$^1$ is hydroxy C$_{2-6}$ alkoxy; R$^2$ is H or methoxy; R$^3$ is H or F; R$^4$ is H; and X is CH.

In another embodiment, R$^1$ is hydroxy C$_{2-6}$ alkoxy; R$^2$ is H; R$^3$ is H or F; R$^4$ is H; and X is CH.

In another embodiment, R$^1$ is —OCH$_2$C(OH)(CH$_3$)$_2$, —(R)—OCH$_2$CH(OH)CH$_3$, and —(S)—OCH$_2$CH(OH) CH$_3$; R$^2$ is H; R$^3$ is F; R$^4$ is H; and X is CH.

In another embodiment, R$^1$ is —OCH$_2$C(OH)(CH$_3$)$_2$, —(R)—OCH$_2$CH(OH)CH$_3$, and —(S)—OCH$_2$CH(OH) CH$_3$; R$^2$ is H; R$^3$ is H; R$^4$ is H; and X is CH.

Some non-limiting examples of the compound disclosed herein, and their pharmaceutically acceptable salts and solvates thereof, are shown in the following:

TABLE 1

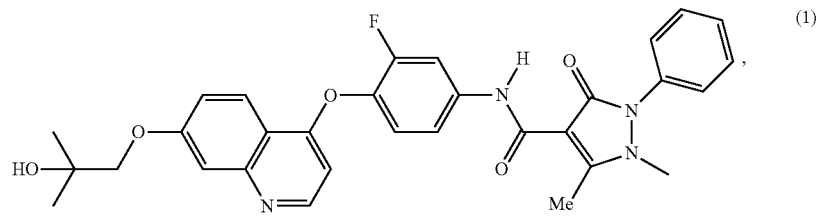

(1)

TABLE 1-continued
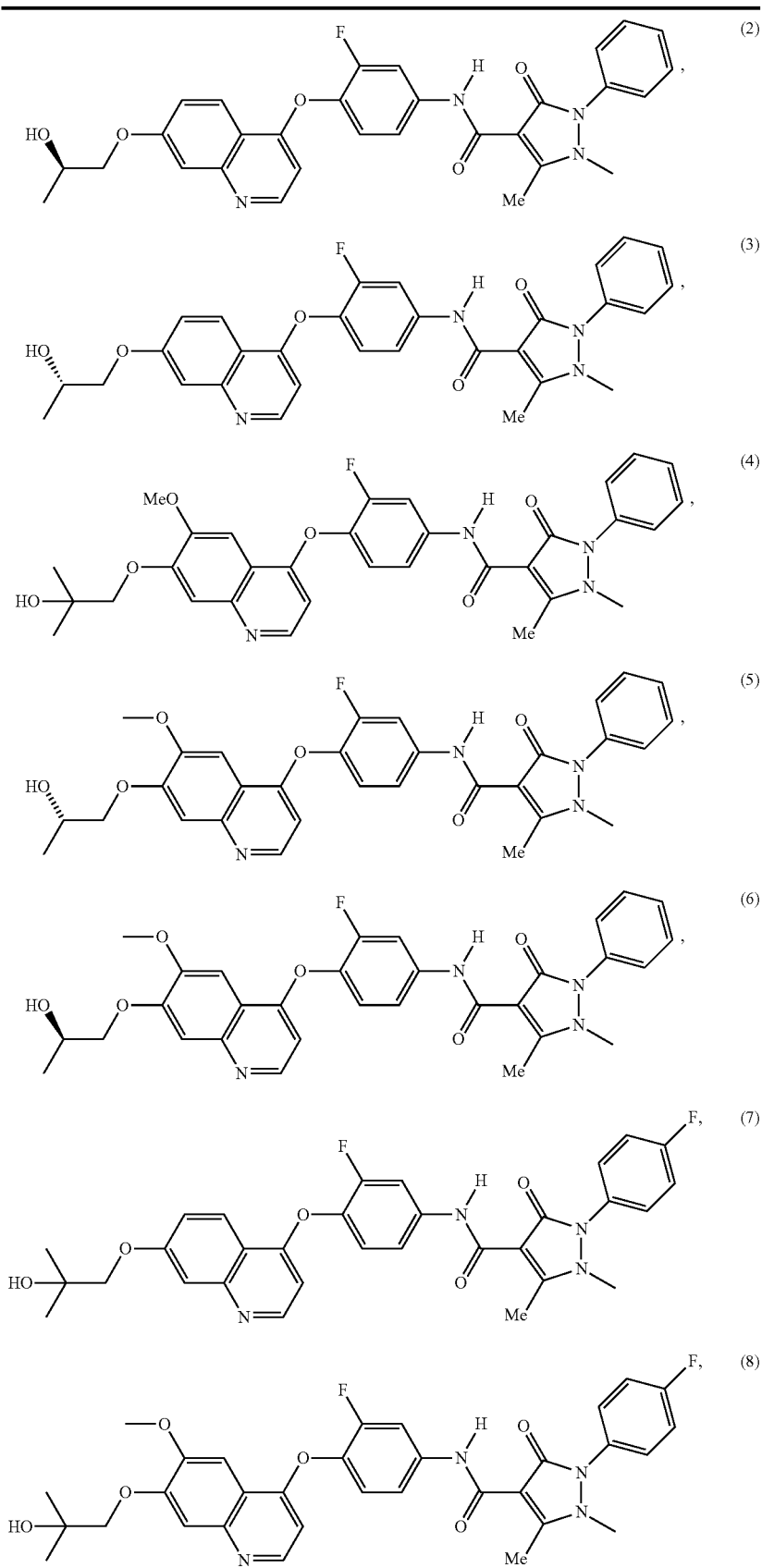

TABLE 1-continued
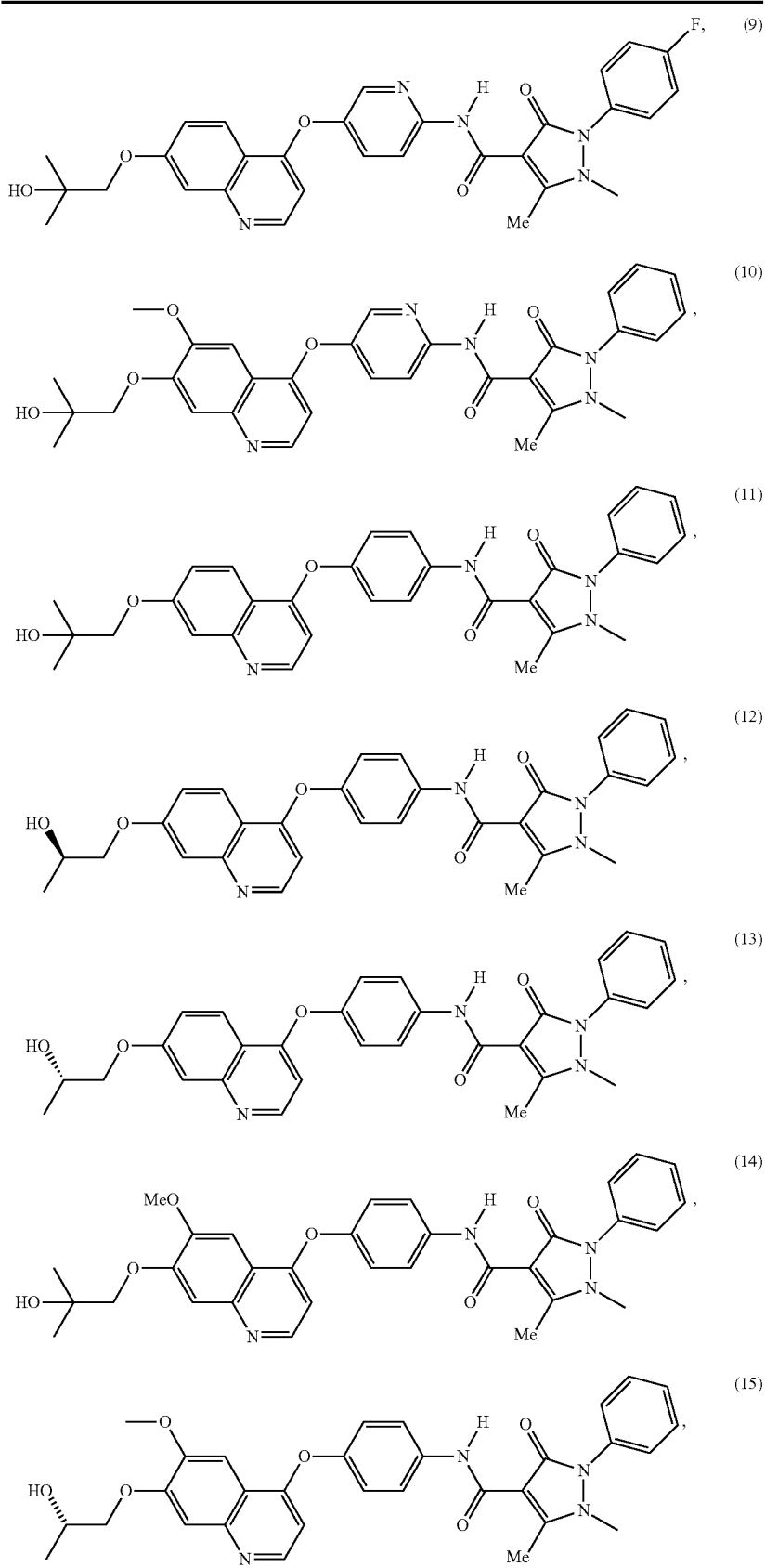

TABLE 1-continued
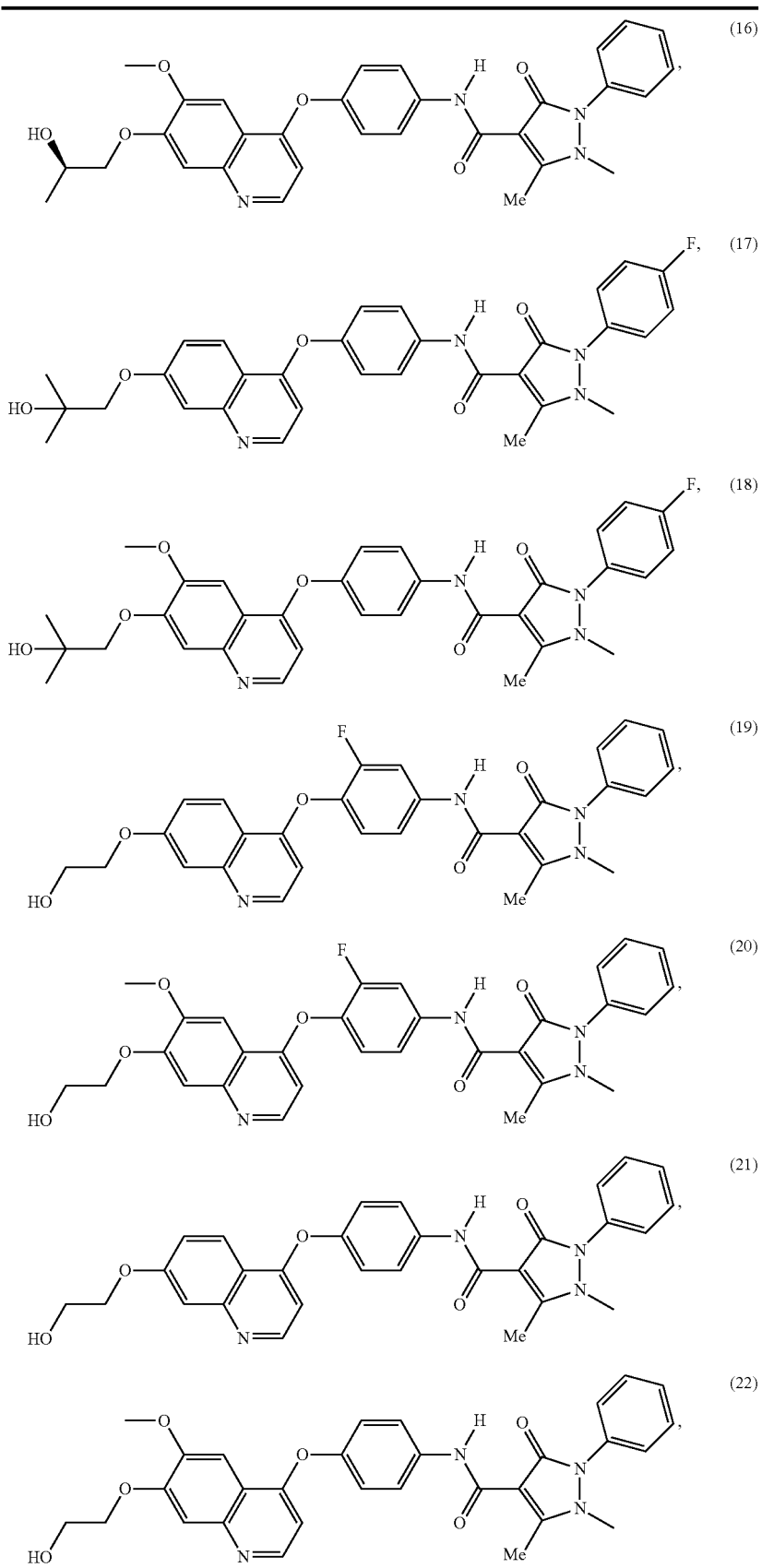

TABLE 1-continued

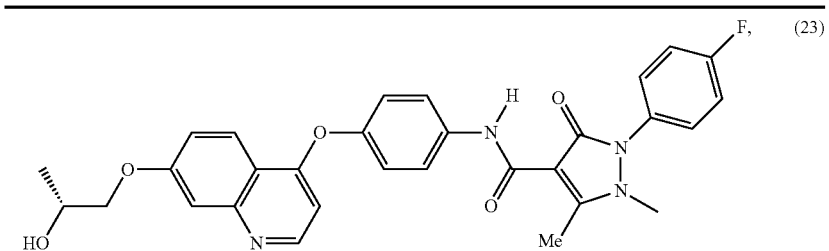 (23)

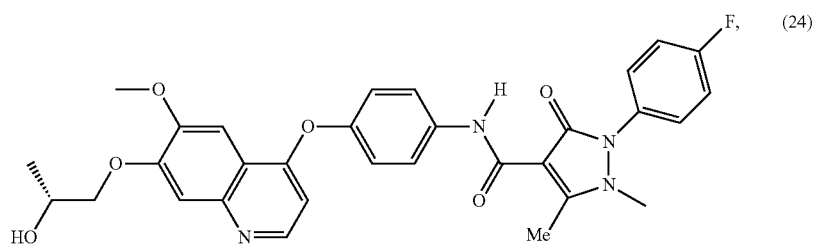 (24)

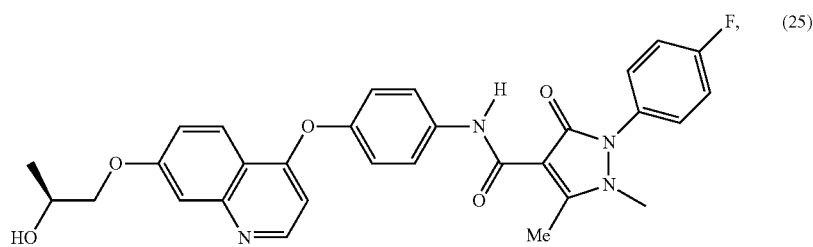 (25)

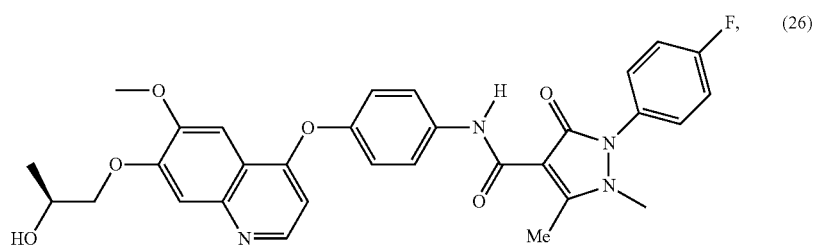 (26)

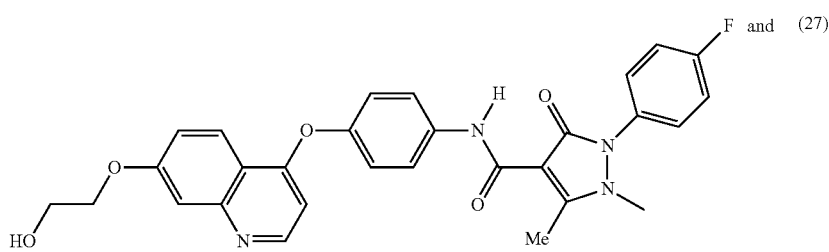 F and (27)

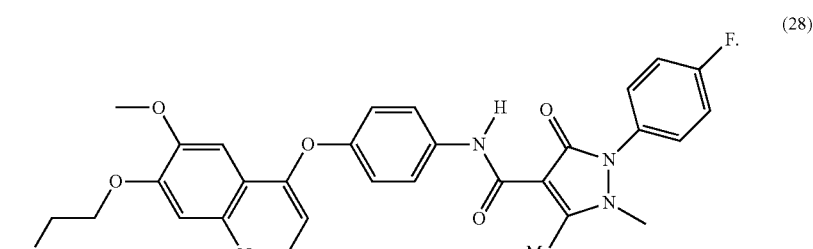 (28)

The present invention also comprises the use of a compound of the invention, or pharmaceutically acceptable salt thereof, in the manufacture of a medicament for the treatment either acutely or chronically of a hyperproliferative disease state and/or an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of protein kinases. The present invention comprises a pharmaceutical composition comprising a therapeutically effective amount of a compound of Formula I in association with at least one pharmaceutically acceptable carrier, adjuvant or diluent.

The present invention also comprises a method of treating hyperproliferating and angiogenesis related disorders in a subject having or susceptible to such disorder, the method comprising treating the subject with a therapeutically effective amount of a compound of Formula I.

Unless otherwise stated, all stereoisomers, geometric isomers, tautomers, solvates, metabolites, salts, and pharmaceutically acceptable prodrugs of the compounds of the invention are within the scope of the invention.

In certain embodiments, the salt is a pharmaceutically acceptable salt. The phrase "pharmaceutically acceptable" indicates that the substance or composition must be compatible chemically and/or toxicologically, with the other ingredients comprising a formulation, and/or the mammal being treated therewith.

The compounds of the invention also include salts of such compounds which are not necessarily pharmaceutically acceptable salts, and which may be useful as intermediates for preparing and/or purifying compounds of Formula I and/or for separating enantiomers of compounds of Formula I.

The desired salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Composition, Formulations and Administration of Compounds of the Invention

According to one aspect, the invention features pharmaceutical compositions that include a compound of formula I, a compound listed in Table 1, and a pharmaceutically acceptable carrier, adjuvant, or vehicle. The amount of compound in the compositions of the invention is such that is effective to detectably inhibit a protein kinase in a biological sample or in a patient.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used. For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polythylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain pacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-200 mg/kg body weight/day of the inhibitor can be administered to a patient receiving these compositions.

Compounds of this invention can be administered as the sole pharmaceutical agent or in combination with one or more other additional therapeutic (pharmaceutical) agents where the combination causes no unacceptable adverse effects. This may be of particular relevance for the treatment of hyperproliferative diseases such as cancer. In this instance, the compound of this invention can be combined with known cytotoxic agents, signal transduction inhibitors, or with other anti-cancer agents, as well as with admixtures and combinations thereof. As used herein, additional therapeutic agents that are normally administered to treat a particular disease, or condition, are known as "appropriate for the disease, or condition, being treated". As used herein, "additional therapeutic agents" is meant to include chemotherapeutic agents and other anti-proliferative agents.

For example, chemotherapeutic agents or other antiproliferative agents may be combined with the compounds of this invention to treat proliferative disease or cancer. Examples of chemotherapeutic agents or other antiproliferative agents include HDAC inhibitors including, but are not limited to, SAHA, MS-275, MGO 103, and those described in WO 2006/010264, WO 03/024448, WO 2004/069823, US 2006/0058298, US 2005/0288282, WO 00/71703, WO 01/38322, WO 01/70675, WO 03/006652, WO 2004/035525, WO 2005/030705, WO 2005/092899, and demethylating agents including, but not limited to, 5-aza-dC, Vidaza and Decitabine and those described in U.S. Pat. No. 6,268,137, U.S. Pat. No. 5,578,716, U.S. Pat. No. 5,919,772, U.S. Pat. No. 6,054,439, U.S. Pat. No. 6,184,211, U.S. Pat. No. 6,020,318, U.S. Pat. No. 6,066,625, U.S. Pat. No. 6,506,735, U.S. Pat. No. 6,221, 849, U.S. Pat. No. 6,953,783, U.S. Ser. No. 11/393,380.

In another embodiment of the present invention, for example, chemotherapeutic agents or other anti-proliferative agents may be combined with the compounds of this invention to treat proliferative diseases and cancer. Examples of known chemotherapeutic agents include, but are not limited to, for example, other therapies or anticancer agents that may be used in combination with the inventive anticancer agents of the present invention and include surgery, radiotherapy (in but a few examples, gamma radiation, neutron beam radiotherapy, electron beam radiotherapy, proton therapy, brachytherapy, and systemic radioactive isotopes, to name a few), endocrine therapy, taxanes (taxol, taxotere etc), platinum derivatives, biologic response modifiers (interferons, interleukins, and tumor necrosis factor (TNF), TRAIL receptor targeting, agents, to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate, Pemetrexed etc), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), Cell cycle inhibitors (KSP mitotic kinesin inhibitors, CENP-E and CDK inhibitors), enzymes (Asparaginase), and hormones (Tamoxifen, Leuprolide, Flutamide, and Megestrol), Gleevec™, adriamycin, dexamethasone, and cyclophosphamide. Antiangiogenic agents (Avastin and others). Monoclonal antibodies (Belimumab (Bnlysta), Brentuximab (Adcetris), Cetuximab (Erbitux), Gemtuzumab (Mylotarg), Ipilimumab (Yervoy), Ofatumumab (Arzerra), Panitumumab (Vectibix), Ranibizumab (Lucertis), Rituximab (Rituxan), Tositumomab (Bexxar), Trastuzumab (Herceptin)). Kinase inhibitors (Imatinib (Gleevec), Sunitinib (Sutent), Sorafenib (Nexavar), Cetuximab (Erbitux), Trastuzumab (Herceptin), Erlotinib (Tarceva), Gefitinib (Iressa), Dasatinib (Sprycel), Nilotinib (Tasigna), Lapatinib (Tykerb), Crizotinib (Xalkori), Ruxolitinib (Jakafi), Vemurafenib (Zelboraf), Vandetanib (Caprelsa), Pazopanib (Votrient), and others). Agents inhibiting or activating cancer pathways such as the mTOR, HIF (hypoxia induced factor) pathways (such as Everolimus and Temsirolimus) and others. For a more comprehensive discussion of updated cancer therapies see, http://www.nci.nih.gov/, a list of the FDA approved oncology drugs at http://www.fda.gov/cder/cancer/druglist-rame.htm, and The Merck Manual, Eighteenth Ed. 2006, the entire contents of which are hereby incorporated by reference.

In another embodiment, the compounds of the present invention can be combined, with cytotoxic anti-cancer agents. Examples of such agents can be found in the 13th Edition of the Merck Index (2001). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other cytotoxic drugs suitable for use with the compounds of the invention include, but are not limited to, those compounds acknowledged to be used in the treatment of neoplastic diseases, such as those for example in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine cladribine, busulfan, diethylstilbestrol, 21, 2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other cytotoxic anti-cancer agents suitable for use in combination with the compounds of the invention also include newly discovered cytotoxic principles such as oxaliplatin, gemcitabine, capecitabine, epothilone and its natural or synthetic derivatives, temozolomide (Quinn et al., J. Clin. Oncology 2003, 21(4), 646-651), tositumomab (Bexxar), trabedectin (Vidal et al., Proceedings of the American Society for Clinical Oncology 2004, 23, abstract 3181), and the inhibitors of the kinesin spindle protein Eg5 (Wood et al., Curr. Opin. Pharmacol. 2001, 1, 370-377).

In another embodiment, the compounds of the present invention can be combined with other signal transduction inhibitors. Examples of such agents include, by no way of limitation, antibody therapies such as Herceptin (trastuzumab), Erbitux (cetuximab), Yervoy (ipilimumab) and pertuzumab. Examples of such therapies also include, by no way of limitation, small-molecule kinase inhibitors such as Imatinib (Gleevec), Sunitinib (Sutent), Sorafenib (Nexavar), Erlotinib (Tarceva), Gefitinib (Iressa), Dasatinib (Sprycel), Nilotinib (Tasigna), Lapatinib (Tykerb), Crizotinib (Xalkori), Ruxolitinib (Jakafi), Vemurafenib (Zelboraf), Vandetanib (Caprelsa), Pazopanib (Votrient), afatinib, alisertib, amuvatinib, axitinib, bosutinib, brivanib, canertinib, cabozantinib, cediranib, crenolanib, dabrafenib, dacomitinib, danusertib, dovitinib, foretinib, ganetespib, ibrutinib, iniparib, lenvatinib, linifanib, linsitinib, masitinib, momelotinib, motesanib, neratinib, niraparib, oprozomib, olaparib, pictilisib, ponatinib, quizartinib, regorafenib, rigosertib, rucaparib, saracatinib, saridegib, tandutinib, tasocitinib, telatinib, tivantinib, tivozanib, tofacitinib, trametinib, vatalanib, veliparib, vismodegib, volasertib, BMS-540215, BMS777607, JNJ38877605, TKI258, GDC-0941 (Folkes, et al., J. Med. Chem. 2008, 51, 5522), BZE235, and others.

In another embodiment, the compounds of the present invention can be combined with inhibitors of histone deacetylase. Examples of such agents include, by no way of limitation, suberoylanilide hydroxamic acid (SAHA), LAQ-824 (Ottmann et al., Proceedings of the American Society for Clinical Oncology 2004, 23, abstract 3024), LBH-589 (Beck et al., Proceedings of the American Society for Clinical Oncology 2004, 23, abstract 3025), MS-275 (Ryan et al., Proceedings of the American Association of Cancer Research 2004, 45, abstract 2452), FR-901228 (Piekarz et al., Proceedings of the American Society for Clinical Oncology 2004, 23, abstract 3028) and MGCDO1 03 (U.S. Pat. No. 6,897,220).

In another embodiment, the compounds of the present invention can be combined with other anti-cancer agents such as proteasome inhibitors, and m-TOR inhibitors. These include, by no way of limitation, bortezomib, and CCI-779 (Wu et al., Proceedings of the American Association of Cancer Research 2004, 45, abstract 3849). The compounds of the present invention can be combined with other anti-cancer agents such as topoisomerase inhibitors, including but not limited to camptothecin.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent. In those compositions which comprise an additional therapeutic agent, that additional therapeutic agent and the compound of this invention may act synergistically.

Uses of the Compounds and Compositions of the Invention

The invention features pharmaceutical compositions that include a compound of formula I, or a compound listed in Table 1, and a pharmaceutically acceptable carrier, adjuvant, or vehicle. The amount of compound in the compositions of the invention is such that is effective to detectably inhibit a protein kinase, such as VEGFR, Axl and c-Met inhibitory activity. The compounds of the invention are useful in therapy as antineoplasia agents or to minimize deleterious effects of VEGFR, Axl and c-Met signaling.

Compounds of the present invention would be useful for, but not limited to, the prevention or treatment of proliferative diseases, condition, or disorder in a patient by administering to the patient a compound or a composition of the invention in an effective amount. Such diseases, conditions, or disorders include cancer, particularly metastatic cancer, atherosclerosis, and lung fibrosis.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

The compounds also would be useful for treatment of ophthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemagimonas, angiofibroma of the nasopharynx and avascular necrosis of bone; and disorders of the female reproductive system such as endometriosis. The compounds are also useful for the treatment of edema, and conditions of vascular hyperpermeability.

The compounds of the present invention are also useful in the treatment of diabetic conditions such as diabetic retinopathy and microangiopathy. The compounds of the present invention are also useful in the reduction of blood flow in a tumor in a subject. The compounds of the present invention are also useful in the reduction of metastasis of a tumor in a subject.

Besides being useful for human treatment, these compounds are also useful for veterinary treatment of companion animals, exotic animals and farm animals, including mammals, rodents, and the like. More preferred animals include horses, dogs, and cats. As used herein, the compounds of the present invention include the pharmaceutically acceptable derivatives thereof.

Where the plural form is used for compounds, salts, and the like, this is taken to mean also a single compound, salt and the like.

The treatment method that includes administering a compound or composition of the invention can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a compound or composition of the invention as a single dosage form or separately from the compound or composition as part of a multiple dosage form. The additional therapeutic agent may be administered at the same time as a compound of the invention or at a different time. In the latter case, administration may be staggered by, for example, 6 hours, 12 hours, 1 day, 2 days, 3 days, 1 week, 2 weeks, 3 weeks, 1 month, or 2 months.

The invention also features a method of inhibiting the growth of a cell that expresses VEGFR, Axl or c-Met, that includes contacting the cell with a compound or composition of the invention, thereby causing inhibition of growth of the cell. Examples of a cell whose growth can be inhibited include: a breast cancer cell, a colorectal cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, or a leukemia cell.

The invention provides a method of inhibiting VEGFR, Axl or c-Met kinase activity in a biological sample that includes contacting the biological sample with a compound or composition of the invention. The term "biological sample" as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly VEGFR, Axl or c-Met kinase activity, in a biological sample is useful for a variety of purposes known to one of skill in the art. Examples of such purposes include, but are not limited to, blood transfusion, organ-transplantation, biological specimen storage, and biological assays.

In certain embodiments of the present invention an "effective amount" or "effective dose" of the compound or pharmaceutically acceptable composition is that amount effective for treating or lessening the severity of one or more of the aforementioned disorders. The compounds and compositions, according to the method of the present invention, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

The compounds of this invention or pharmaceutical compositions thereof may also be used for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a compound of this invention.

Suitable coatings and the general preparation of coated implantable devices are described in U.S. Pat. Nos. 6,099, 562; 5,886,026; and 5,304,121, the contents of each of which are incorporated by reference herein. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics into the composition. Implantable devices coated with a compound of this invention are another embodiment of the present invention. The compounds may also be coated on implantable medical devices, such as beads, or co-formulated with a polymer or other molecule, to provide a "drug depot" thus permitting the drug to be released over a longer time period than administration of an aqueous solution of the drug.

General Synthetic Procedures

In order to illustrate the invention, the following examples are included. However, it is to be understood that these examples do not limit the invention and are only meant to suggest a method of practicing the invention.

Generally, the compounds in this invention may be prepared by methods described herein, wherein the substituents are as defined for formulas I, above, except where further noted. The following non-limiting schemes and examples are presented to further exemplify the invention. Persons skilled in the art will recognize that the chemical reactions described herein may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Arco Chemical Company and Alfa Chemical Company, Shanghai Medpep. Co Ltd, Aladdin-Shanghai Jinchun Reagents, Ltd, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, TainjinYuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous $CH_2Cl_2$ and $CHCl_3$ were obtained by refluxing the solvent with $CaH_2$. EtOAc, PE, hexanes, DMA and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were recorded with a Bruker 400 MHz spectrometer at ambient temperature. $^1$H NMR spectra were obtained as $CDCl_3$, $d_8$-DMSO, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were generally determined on an Agilent 1200 Series LCMS (Zorbax SB-C18, 2.1×30 mm, 4 micorn, 10 minutes run, 0.6 mL/min flow rate, 5 to 95% (0.1% formic acid in $CH_3CN$) in (0.1% formic acid in $H_2O$)) with UV detection at 210/254 nm and a low resonance electrospray mode (ESI).

Purities of compounds were assessed by Agilent 1100 Series high performance liquid chromatography (HPLC) with UV detection at 210 nm and 254 nm. Column was normally operated at 40° C.

The following abbreviations are used throughout the specification:
HOAc acetic acid
MeCN, $CH_3CN$ acetonitrile
$NH_3$ ammonia
$NH_4Cl$ ammonium chloride
HBTA  O-benzotriazol-1-yl-N,N,N',N'-tetramethyluronium hexafluorophosphate
HATU  O-(7-azabenzotriazol-1-yl)-N,N,N',N'-tetramethyluronium hexafluorophosphate
PyBop  benzotriazol-1-yl-oxy-tripyrrolidino-phosphonium hexafluorophosphate
$Pd_2(dba)_3$ bis(dibenzylideneacetone) palladium
BINAP 2,2'-bis(diphenylphosphino)-1,1'-binaphthyl
TEAC bis(tetra-ethylammonium)carbonate
$BBr_3$ boron tribromide
BSA bovine serum albumin
BOC, Boc butyloxycarbonyl
$Ca(SO_3CF_3)_2$ calcium trifluoromethyl sulfonate
$Cs_2CO_3$ cesium carbonate
$CHCl_3$ chloroform
$CDCl_3$ chloroform deuterated
Cu copper
CuI copper(I) iodide Et₂O diethyl ether
DBU 1,8-diazabicyclo[5 A0]undec-7-ene
DIBAL diisobutylaluminum hydride
DIAD diisopropyl azodicarboxylate
DIEA or DIPEA diisopropylethylamine
DEAD dimethyl azodicarboxylate
DMF dimethylformamide
DMAP 4-dimethylaminopyridine
DMSO dimethylsulfoxide
EDC, EDCI 1-(3-dimethylaminopropyl)-3-ethylcarbodiimide hydrochloride dppa diphenylphosphoryl azide
EtOAc, EA, ethyl acetate
FBS fetal bovine serum
g gram
h hour
HBr hydrobromic acid
HCl hydrochloric acid
HOBt 1-hydroxybenzotriazole hydrate
H₂ hydrogen
H₂O₂ hydrogen peroxide
Fe iron
LiHMDS lithium bis(trimethylsilyl)-amide
LDA Lithium diisopropylamide
MCPBA meta-chloroperbenzoic acid
MgSO₄ magnesium sulfate
MeOH, CH₃OH methanol
MeI methyl iodide
2-MeTHF 2-methyl tetrahydrofuran
CH₂Cl₂, DCM methylene chloride
NMP N-methylpyrrolidinone
mL, ml milliliter
N₂ nitrogen
Pd/C palladium on carbon
Pd(OAc)₂ palladium acetate
Pd(OH)₂ palladium hydroxide
Pd(PPh₃)₄ palladium tetrakis triphenylphosphine
Pd(dppf)Cl₂ 1,1-bis(diphenylphosphino)ferrocene palladium chloride
PE petroleum ether (60-90° C.)
PBS phosphate buffered saline
POCl₃ phosphorous oxychloride
K₂CO₃ potassium carbonate
KOH potassium hydroxide
RT rt r.t. room temperature
Rt retention time
NaHCO₃ sodium bicarbonate
NaBH₄ sodium borohydride
NaBH₃CN sodium cyanoborohydride
NaOtBu sodium tert-butoxide
NaOH sodium hydroxide
NaClO₂ sodium chlorite
NaCl sodium chloride
NaH₂PO₄ sodium biphosphate
NaH sodium hydride
NaI sodium iodide
Na₂SO₄ sodium sulfate
TBTU O-benzotriazol-1-yl-N,N,N',N'-tetramethyluronium tetrafluoroborate
THF tetrahydrofuran
Et₃N, TEA triethylamine
TFA trifluoroacetic acid
P(t-bu)₃ tri(tert-butyl)phosphine
H₂O water

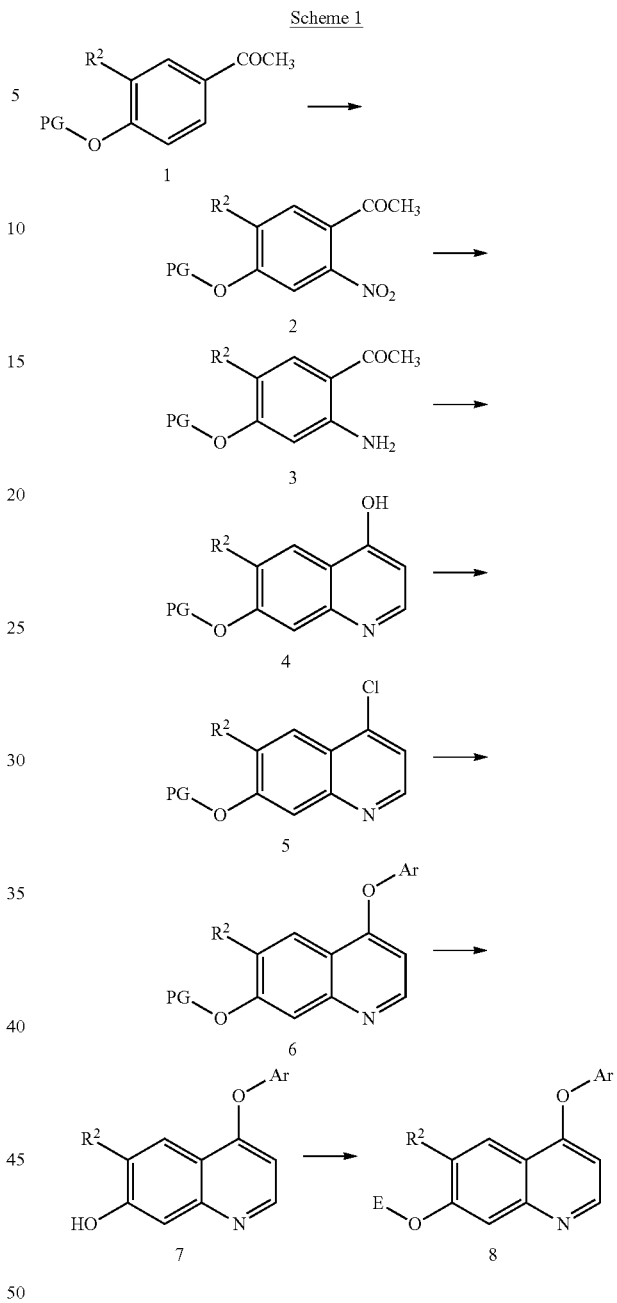

Scheme 1

PG: Protecting group; Ar: substituted aryl or heteroaryl; E-O: group defined by $R^1$ The desired kinase inhibitor quinoline 8 can be prepared by the process illustrated in Scheme 1, wherein $R^1$, $R^2$, $R^3$, $R^4$ and X are defined herein. The substituted aryl 1 is nitrated to give compound 2 by a suitable nitration reagent such as HNO₃ at appropriate temperature such as 0° C. The NO₂ group is then reduced by a reducing reagent such as Fe or Zn powder, or reducing agent SnCl₂, or under hydrogenation condition in the presence of Pd catalyst such as Pd/C. Aniline 3 is condensed with a formate (for example, ethyl formate) under basic condition to give substituted quinoline 4. The hydroxy group in 4 is converted to Cl using a chlorinating agent such as POCl₃ or SOCl₂ under heating conditions to afford quinoline chloride 5. Coupling of 5 with appropriate aryl derivatives (with a free OH group) yields substituted diaryl ethers 6. The protecting group PG is removed to provide compound 7, which is condensed with E-L (L=a suitable leaving group such as OMs, Cl, Br or I, E-O is a moiety defined by $R^1$) to afford compound 8.

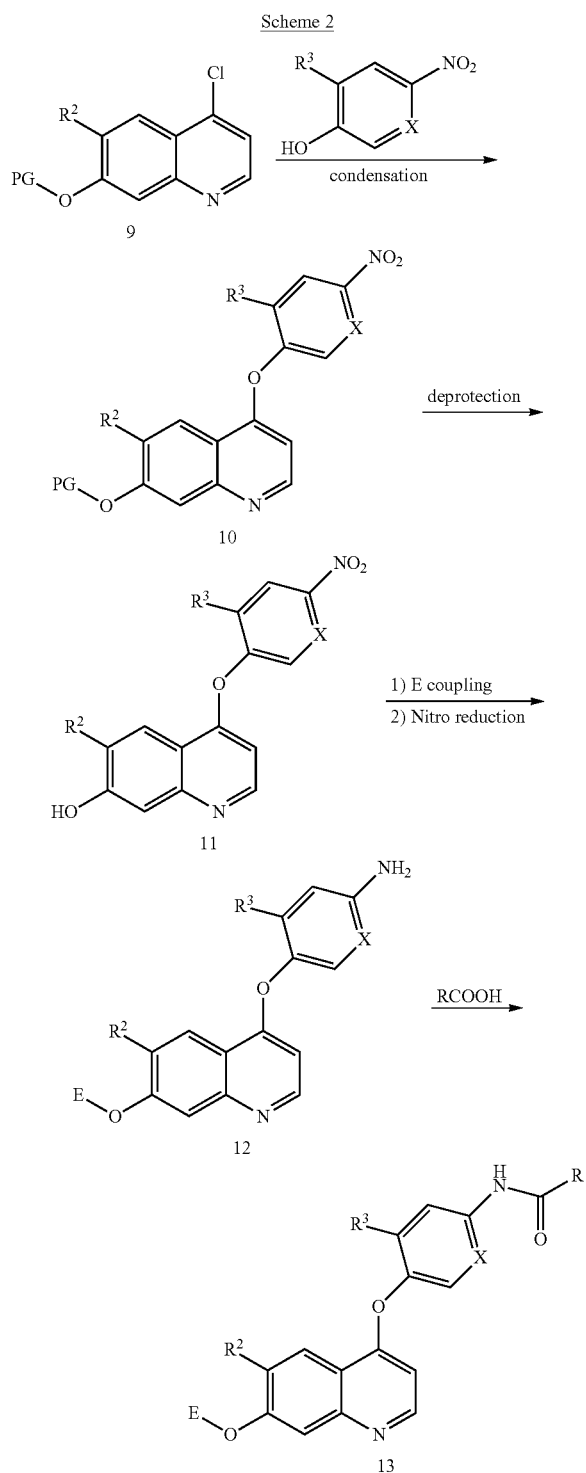

Scheme 2

Alternatively, kinase inhibitors 13 can be prepared using a process as demonstrated in Scheme 2. Condensation of 9 under heating conditions with a nitro-aryl derivative gives compound 10. Deprotection to remove the protecting group PG leads to compound 11. Attachment of E group through a coupling process followed by the reduction of nitro group affords compound 12. Coupling of aniline 12 with an acid in the presence of coupling reagent such as EDCI or HATU furnishes desired kinase inhibitors 13.

EXAMPLES

Example 1

N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide

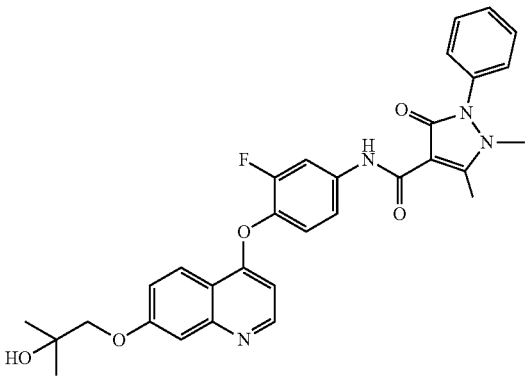 [SMILES: Cc1c(C(=O)Nc2ccc(Oc3ccnc4cc(OCC(C)(C)O)ccc34)c(F)c2)c(=O)n(-c2ccccc2)n1C]

Step 1) 5-(((3-(benzyloxy)phenyl)amino)methylene)-2,2-dimethyl-1,3-dioxane-4,6-dione To a solution of 3-(Benzyloxy)benzenamine (970 g, 4.9 mol, Wuhan Xinghuayuan Tech. Co. Ltd.) and 2,2-dimethyl-1,3-dioxane-4,6-dione (842.3 g, 5.8 mol) in anhydrous EtOH (970 mL) was added triethoxymethane (865.7 g, 5.8 mol). The suspension was heated to reflux for 1 hour. The reaction mixture was then cooled to room temperature, and continued to stir for additional 2 hours. The suspension was filtered, and the solid was stirred in anhydrous EtOH (970 mL) for 2 hours, collected by filtration. The solid was dried in vacuo at 45° C. to give the title compound as a pale yellow solid (1.7 kg, 96.5%).

MS (ESI, neg. ion) m/z: 352.3 [M−1];

$^1$H NMR (400 MHz, DMSO-$d_6$): δ 1.71 (s, 6H), 5.16 (s, 2H), 6.91 (dd, J=2.0 Hz, J=8.0 Hz, 1H), 7.13 (dd, J=1.6 Hz, J=8.0 Hz, 1H), 7.32-7.36 (m, 3H), 7.39-7.43 (m, 2H), 7.48 (d, J=7.2 Hz, 1H), 8.63 (d, J=14.4 Hz, 1H), 11.23 (d, J=14.4 Hz, 1H).

Step 2) 7-(benzyloxy)quinolin-4-ol

A solution of 5-((3-(Benzyloxy)phenylamino)methylene)-2,2-dimethyl-1,3-dioxane-4,6-dione (300 g, 849.8 mol) in 1,2-dichlorobenzene (3 L, Aladdin) was heated to reflux for 5 hours. The reaction mixture was cooled to room temperature, followed by further cooling in an ice bath for 2 hours. The solid was collected through filtration, stirred with MeOH (300 mL) at room temperature for 2 hours. The solid was collected through filtration and dried in vacuo at 45° C. to afford the title compound as a pale solid (103 g, 48.5%).

MS (ESI, pos. ion) m/z: 252.2 [M+1];

¹H NMR (400 MHz, DMSO-d₆): δ 5.23 (s, 2H), 5.98 (d, J=7.2 Hz, 1H), 7.02 (t, 2H), 7.41 (t, 1H), 7.45 (t, J=6.8 Hz, J=7.6 Hz, 2H), 7.52 (d, J=7.6 Hz, 2H), 7.84 (t, J=6.4 Hz, J=6.0 Hz, 1H), 8.03 (d, J=9.2 Hz, 1H), 11.60 (s, 1H).

Step 3) 7-(benzyloxy)-4-chloroquinoline

To a suspension of 7-(benzyloxy)quinolin-4-ol (72 g, 287 mmol) in toluene (134 mL) was added phosphoryl trichloride (44 g, 287 mmol, Tianjin FuChen Chem. Co. Ltd.). The suspension was heated to 120° C. for 1 hour. The reaction mixture was then cooled to 70° C. and diluted with EtOAc (600 mL). The resulted mixture was stirred for 30 minutes while cooling down to 15° C. using an ice bath. The mixture was neutralized with 3 M NaOH aqueous solution to pH 7~8 while maintaining the temperature of the solution under 20° C. The aqueous layer was separated and extracted with EtOAc (200 mL). The combined organic layers were washed with brine (200 mL), dried over anhydrous Na₂SO₄ and concentrated in vacuo to give the title compound as a pale yellow solid (70.8 g, 91.6%).

MS (ESI, pos. ion) m/z: 270.1 [M+1];

¹H NMR (400 MHz, DMSO-d₆): δ 5.31 (s, 2H), 7.35 (t, 1H), 7.42 (t, J=7.2 Hz, J=7.6 Hz, 2H), 7.47 (dd, J=2.8 Hz, J=9.2 Hz, 1H), 7.52 (d, J=7.6 Hz, 2H), 7.13 (t, J=4.8 Hz, J=4.0 Hz, 2H), 8.11 (d, J=9.6 Hz, 1H), 8.75 (d, J=4.8 Hz, 1H).

Step 4) 7-(benzyloxy)-4-(2-fluoro-4-nitrophenoxy)quinoline

To a suspension of 7-(benzyloxy)-4-chloroquinoline (45 g, 0.17 mol) and 2-fluoro-4-nitrophenol (28.9 g, 0.18 mol) in toluene (42 mL) was added DIPEA (25.9 g, 0.2 mol). The suspension was heated to 115° C. for 12 hours and then concentrated in vacuo. The residue was diluted with EtOH (45 mL), stirred at 60° C. for 30 minutes, and then allowed to cool down to 0° C. in an ice bath. The solid was collected through filtration, dried in vacuo at 45° C. for 24 hours to afford the title compound as a light grey solid (59.1 g, 91%)

MS (ESI, pos. ion) m/z: 391.1 [M+1];

¹H NMR (400 MHz, DMSO-d₆): δ 5.33 (s, 2H), 6.79 (d, J=4.8 Hz, 1H), 7.37 (t, 1H), 7.39-7.44 (m, 3H), 7.52-7.57 (m, 3H), 7.64 (t, J=8.4 Hz, J=8.8 Hz, 1H), 8.16-8.21 (m, 2H), 8.46 (dd, J=2.8 Hz, J=10.4 Hz, 1H), 8.71 (d, J=4.8 Hz, 1H).

Step 5) 4-(2-fluoro-4-nitrophenoxy)quinolin-7-ol

A suspension of 7-(benzyloxy)-4-(2-fluoro-4-nitrophenoxy)quinoline (100 g, 256.4 mmol) in dioxane (425 mL) and conc. HCl (425 mL, 5.1 mol) was stirred at 100° C. for 24 hours. The reaction mixture was then cooled to room temperature and solid was collected through filtration. The solid was then suspended in anhydrous EtOH (100 mL) and stirred for 2 hours. The solid was collected and dried in vacuo at 60° C. for 12 hours to give the title compound as a pale solid (73.3 g, 85%).

MS (ESI, pos. ion) m/z: 301 [M+1];

¹H NMR (400 MHz, DMSO-d₆): δ 7.06-7.07 (d, J=6.8 Hz, 1H), 7.51-7.54 (m, 1H), 7.71 (s, 1H), 7.89-7.94 (m, 1H), 8.28-8.30 (d, J=8.8 Hz, 1H), 8.41-8.43 (d, J=9.6 Hz, 1H), 8.51-8.54 (d, J=10 Hz, 1H), 8.94-8.96 (d, J=6.4 Hz, 1H), 12.00 (s, 1H).

Step 6) 1-((4-(2-fluoro-4-nitrophenoxy)quinolin-7-yl)oxy)-2-methylpropan-2-ol

To a solution of 4-(2-fluoro-4-nitrophenoxy)quinolin-7-ol (60 g, 0.2 mol) in THF/H₂O (1 L, THF/H₂O=1:1, v/v) was added NaOH (24 g, 0.6 mol) at room temperature, followed by isobutylene oxide (144 g, 2 mol). The reaction was stirred at 45° C. for 10 hours, and then diluted with EtOAc (1 L). The resulted solution was washed with 1 M NaOH aqueous solution (500 mL×4). The organic layer was separated, dried over Na₂SO₄ and concentrated in vacuo. The residue was washed with 500 mL of petroleum ether, and collected through filtration to give the title compound as a light yellow solid (31.6 g, 42.5%).

MS (ESI, pos. ion) m/z: 373.1 [M+1];

¹H NMR (400 MHz, CDCl₃): δ 1.41 (s, 6H), 2.28 (s, 1H), 3.98 (s, 2H), 6.53-6.54 (d, J=5.2 Hz, 1H), 7.26-7.36 (m, 2H), 7.45-7.46 (d, J=2.4 Hz, 1H), 8.12-8.20 (m, 3H), 8.69-8.70 (d, J=4.8 Hz, 1H).

Step 7) 1-((4-(4-amino-2-fluorophenoxy)quinolin-7-yl)oxy)-2-methylpropan-2-ol

To a mixture of 1-((4-(2-fluoro-4-nitrophenoxy)quinolin-7-yl)oxy)-2-methylpropan-2-ol (10.04 g, 27 mmol) and HCOOK (15.87 g, 189 mmol) in THF/H₂O (54 mL, THF/H₂O=4:1) was added catalytic amount of Pd/C (5%, 53%~55% water content, w/w). The reaction was stirred at 45° C. for 5 hours, and then diluted with THF/H₂O (40 mL, v/v=1:1). The resulted mixture was filtered and the filtrate was concentrated in vacuo. The residue was washed with EtOH/H₂O (30 mL×3, v/v=5:1), and dried in vacuo at 45° C. for 24 hours to give the title compound as a light gray solid (8.1 g, 87%).

MS (ESI, pos. ion) m/z: 343.1 [M+1];

¹H NMR (400 MHz, CDCl₃): δ 1.40 (s, 6H), 3.81 (s, 2H), 3.96 (s, 2H), 6.39-6.40 (d, J=4.0 Hz, 1H), 6.49-6.57 (m, 2H), 7.00-7.05 (d, J=2.0 Hz, 1H), 7.25-7.27 (m, 1H), 7.39 (s, 1H), 8.27-8.30 (d, J=6.0 Hz, 1H), 8.57-8.58 (d, J=4.0 Hz, 1H).

Step 8) N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide To a solution of 1-((4-(4-amino-2-fluorophenoxy)quinolin-7-yl)oxy)-2-methylpropan-2-ol (5 g, 14.6 mmol), 1,5-dimethyl-3-oxo-2-phenyl-2,3-dihydro-1H-pyrazole-4-carboxylic acid (3.46 g, 14.9 mmol) and HOAT (0.39 g, 2.9 mmol) in dichloromethane (30 mL) was added EDCI (3.35 g, 17.5 mmol). The mixture was stirred at 41° C. for 6 hours, cooled to room temperature and diluted with ethyl acetate (30 mL). The resulted suspension was filtered, and the solid was washed with 95% ethanol (50 mL×2). The solid was collected through filtration and dried in vacuo at 45° C. for 6 hours to give the title compound as a white solid (6.35 g, 78%).

MS (ESI, pos. ion) m/z: 557.2 [M+1]; LC-MS Rt: 2.905 min;

¹H NMR (400 MHz, CDCl₃): δ 10.89 (s, 1H), 8.60 (d, J=5.2 Hz, 1H), 8.30 (d, J=9.2 Hz, 1H), 7.94-7.91 (dd, J=12.4 Hz, 1H), 7.59-7.55 (m, 2H), 7.51-7.47 (m, 1H), 7.40-7.36 (m, 3H), 7.32-7.26 (m, 1H), 7.28 (s, 1H), 6.43-6.41 (d, J=5.3 Hz, 1H), 3.97 (s, 2H), 3.38 (s, 3H), 2.81 (s, 3H), 2.34 (s, 1H), 1.41 (s, 6H).

Example 2

(R)—N-(3-fluoro-4-((7-(2-hydroxypropoxy)quinolin-4-yl)oxy)phenyl)-1,5-dimethyl-3-oxo-2-phenyl-2,3-dihydro-1H-pyrazole-4-carboxamide

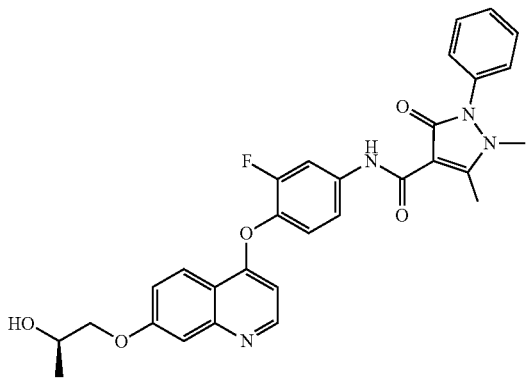 [SMILES: Cc1c(C(=O)Nc2ccc(Oc3ccnc4cc(OC[C@H](C)O)ccc34)c(F)c2)c(=O)n(-c2ccccc2)n1C]

Step 1) 4-(4-amino-2-fluorophenoxy)quinolin-7-ol

To a mixture of 7-(benzyloxy)-4-(2-fluoro-4-nitrophenoxy)quinoline (16.38 g, 42 mmol) and HCOONH$_4$ (26.46 g, 420 mmol) in a mixture solution of EtOH/H$_2$O (84 mL, v/v=4:1) was added a catalytic amount of Pd/C (0.50 g, 5% amount, 53%~55% water content, w/w). The reaction was stirred at 30° C. for 24 hours, and was monitored by LC-MS. After the complete consumption of 7-(benzyloxy)-4-(2-fluoro-4-nitrophenoxy)quinoline, 6 M HCl (80 mL) was added to the reaction mixture until the solid was dissolved. The resulted solution was filtered. Saturated aqueous NaHCO$_3$ solution (210 mL) was added to the filtrate to adjust the final pH to 6.0~6.5 followed by the addition of a mixture of water (20 mL) and CH$_2$Cl$_2$ (50 mL). The resulted mixture was stirred at room temperature for 4 hours. The solid was collected by filtration, washed with a mixture of MeOH/DCM (50 mL, v/v=1/1), and dried in vacuo at 45° C. to give the title compound as a light yellow solid (11.0 g, 92%).

MS (ESI, pos. ion) m/z: 271.2 [M+1]; LC-MS Rt: 2.421 min;

$^1$H NMR (400 MHz, DMSO-d$_6$): δ 5.47 (s, 2H), 6.30-6.31 (d, J=4 Hz, 1H), 6.45-6.47 (d, J=8 Hz, 1H), 6.53-6.56 (d, J=12 Hz, 1H), 7.04-7.08 (t, 1H), 7.17-7.19 (d, J=8 Hz, 1H), 7.23 (s, 1H), 8.14-8.16 (d, J=8 Hz, 1H), 8.50-8.51 (d, J=4 Hz, 1H), 10.28 (s, 1H).

Step 2) N-(3-fluoro-4-((7-hydroxyquinolin-4-yl)oxy)phenyl)-1,5-dimethyl-3-oxo-2-phenyl-2,3-dihydro-1H-pyrazole-4-carboxamide To a solution of 4-(4-amino-2-fluorophenoxy)quinolin-7-ol (10 g, 37.0 mmol), 1,5-dimethyl-3-oxo-2-phenyl-2,3-dihydro-1H-pyrazole-4-carboxylic acid (10 g, 44.4 mmol), HOAT (0.5 g, 3.7 mmol) in DMF (50 mL) and toluene (30 mL) was added EDCI (8.5 g, 44.4 mmol). The reaction was stirred at 45° C. overnight, then diluted with water (100 mL) and continued to stir at room temperature for 2 hours. The solid was collected through filtration, washed with a mixture of 95% EtOH (50 mL) and DCM (25 mL), and then treated with 3 M hydrochloric acid (10.5 mL). The resulted solid was collected and was recrystallized in a mixture of 95% EtOH and H$_2$O (90 mL, EtOH/H$_2$O=5:1, v/v) to give the title compound as a white solid (11.7 g, 60.8%).

MS (ESI, pos. ion) m/z: 485.2 [M+1];

$^1$H NMR (400 MHz, DMSO-d$_6$): δ 2.72 (s, 3H), 3.38 (s, 3H), 6.40 (s, 1H), 7.21-7.28 (m, 2H), 7.36-7.46 (m, 4H), 7.53-7.60 (m, 3H), 8.01 (d, J=12.4 Hz, 1H), 8.20 (d, J=8.0 Hz, 1H), 8.55 (s, 1H), 10.32 (s, 1H), 10.98 (s, 1H).

Step 3) (R)—N-(3-fluoro-4-((7-(2-hydroxypropoxy)quinolin-4-yl)oxy)phenyl)-1,5-dimethyl-3-oxo-2-phenyl-2,3-dihydro-1H-pyrazole-4-carboxamide To a mixture of N-(3-fluoro-4-((7-hydroxyquinolin-4-yl)oxy)phenyl)-1,5-dimethyl-3-oxo-2-phenyl-2,3-dihydro-1H-pyrazole-4-carboxamide (100 mg, 0.21 mmol) and Cs$_2$CO$_3$ (337 mg, 1.03 mmol) in 10 mL DMF was added (R)-2-methyloxirane (5 mL, 71.60 mmol). The reaction was warmed to 40° C. and stirred for two days. The mixture was concentrated in vacuo and the residue was purified by a silica gel column chromatography (1:15 (v/v) MeOH/DCM) to give the title compound as a white solid (60 mg, 54%).

MS (ESI, pos. ion) m/z: 543.2 [M+1]; LC-MS Rt: 2.983 min;

$^1$H NMR (400 MHz, CDCl$_3$): δ 1.33-1.36 (d, J=6.3 Hz, 3H), 2.80 (s, 3H), 3.37 (s, 3H), 3.95-4.02 (m, 1H), 4.09-4.15 (m, 1H), 4.25-4.35 (m, 1H), 6.40-6.50 (d, J=4.8 Hz, 1H), 7.13-7.21 (t, J=8.5 Hz, 1H), 7.22-7.28 (m, 1H), 7.28-7.34 (m, 1H), 7.34-7.39 (m, 2H), 7.39-7.42 (s, 1H), 7.43-7.52 (m, 1H), 7.53-7.60 (m, 2H), 7.89-7.96 (d, J=12.5 Hz, 1H), 8.26-8.31 (d, J=9.0 Hz, 1H), 8.57-8.61 (d, J=5.0 Hz, 1H), 10.88 (s, 1H).

Example 3

(S)—N-(3-fluoro-4-((7-(2-hydroxypropoxy)quinolin-4-yl)oxy)phenyl)-1,5-dimethyl-3-oxo-2-phenyl-2,3-dihydro-1H-pyrazole-4-carboxamide

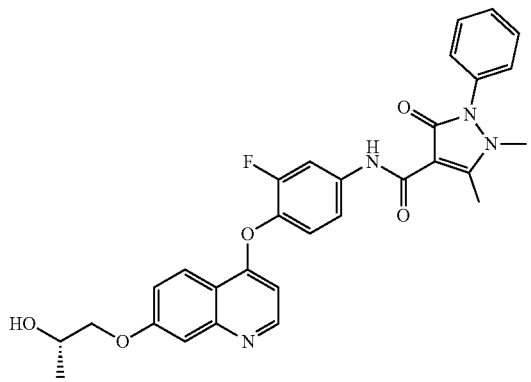

The title compound was prepared according to the procedure described in Example 2 by using N-(3-fluoro-4-((7-hydroxyquinolin-4-yl)oxy)phenyl)-1,5-dimethyl-3-oxo-2-phenyl-2,3-dihydro-1H-pyrazole-4-carboxamide (1.00 g, 2.07 mmol), (S)-2-methyloxirane (1.44 mL, 20.70 mmol) and Cs$_2$CO$_3$ (1.35 g, 4.14 mmol) in 10 mL DMF. The title compound was obtained as a white solid (663 mg, 55%).

MS (ESI, pos. ion) m/z: 543.2 [M+1]; LC-MS Rt: 2.935 min;

$^1$H NMR (400 MHz, CDCl$_3$): δ 1.30-1.40 (d, J=6.3 Hz, 3H), 2.79 (s, 3H), 3.36 (s, 3H), 3.96-4.02 (dd, J$_1$=7.5 Hz, $J_2$=9.5 Hz, 1H), 4.08-4.14 (dd, $J_1$=3.3 Hz, $J_2$=9.5 Hz, 1H), 4.25-4.34 (m, 1H), 6.40-6.50 (dd, $J_1$=1.0 Hz, $J_2$=5.2 Hz, 1H), 7.13-7.19 (t, J=8.6 Hz, 1H), 7.22-7.26 (dd, $J_1$=2.5 Hz, $J_2$=9.2 Hz, 1H), 7.28-7.33 (m, 1H), 7.34-7.37 (m, 2H), 7.39-7.41 (d, J=2.5 Hz, 1H), 7.45-7.50 (m, 1H), 7.53-7.59 (m, 2H), 7.90-7.95 (dd, $J_1$=2.5 Hz, $J_2$=12.5 Hz, 1H), 8.26-8.30 (d, J=9.2 Hz, 1H), 8.57-8.60 (d, J=5.3 Hz, 1H), 10.88 (s, 1H).

Example 4

N-(3-fluoro-4-((7-(2-hydroxy-2-methylpropoxy)-6-methoxyquinolin-4-yl)oxy)phenyl)-1,5-dimethyl-3-oxo-2-phenyl-2,3-dihydro-1H-pyrazole-4-carboxamide

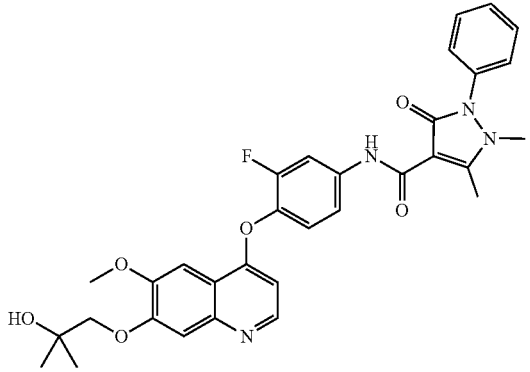 [SMILES: COc1cc2c(Oc3ccc(NC(=O)c4c(C)n(C)n(-c5ccccc5)c4=O)cc3F)ccnc2cc1OCC(C)(C)O]

To a mixture of N-(3-fluoro-4-((7-hydroxy-6-methoxyquinolin-4-yl)oxy)phenyl)-1,5-dimethyl-3-oxo-2-phenyl-2,3-dihydro-1H-pyrazole-4-carb oxamide (5.00 g, 9.73 mmol) and $Cs_2CO_3$ (1.35 g, 4.14 mmol) in DMF/t-BuOH (15.60 mL/3.90 mL) was added isobutylene oxide (8.60 mL, 97.30 mmol). The reaction was warmed to 50° C. and stirred for three days. The reaction mixture was concentrated in vacuo and purified by a silica gel column chromatography (1:25 (v/v)=methanol/dichloromethane) to give the title compound as a white solid (2.28 g, 40%).

MS (ESI, pos. ion) m/z: 587.2 [M+1]; LC-MS Rt: 2.911 min;

$^1$H NMR (400 MHz, $CDCl_3$): δ 1.41 (s, 6H), 2.79 (s, 3H), 3.36 (s, 3H), 3.99 (s, 2H), 4.01 (s, 3H), 6.41-6.46 (d, J=5.1 Hz, 1H), 7.14-7.22 (t, J=8.6 Hz, 1H), 7.29-7.34 (m, 1H), 7.34-7.39 (m, 2H), 7.39-7.43 (s, 1H), 7.45-7.51 (m, 1H), 7.53-7.60 (m, 3H), 7.90-7.97 (dd, $J_1$=2.3 Hz, $J_2$=12.5 Hz, 1H), 8.46-8.50 (d, J=5.3 Hz, 1H), 10.89 (s, 1H).

Example 5

N-(3-fluoro-4-((7-(2-hydroxy-2-methylpropoxy) quinolin-4-yl)oxy)phenyl)-1,5-dimethyl-3-oxo-2-phenyl-2,3-dihydro-1H-pyrazole-4-carboxamide hydrochloride

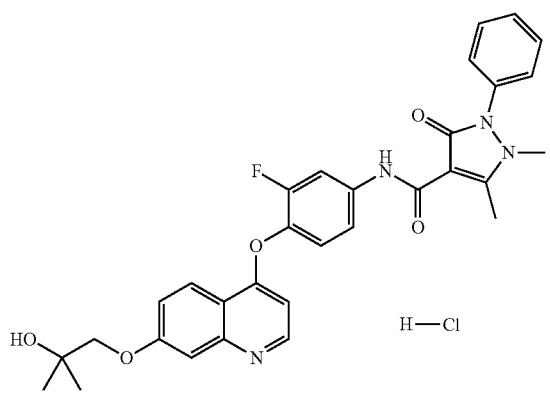 [SMILES: Cc1c(C(=O)Nc2ccc(Oc3ccnc4cc(OCC(C)(C)O)ccc34)c(F)c2)c(=O)n(-c2ccccc2)n1C ; Cl]

To a solution of N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide (300 mg, 0.54 mmol) in DCM/MeOH (30 mL, v/v=1:2) was added 1 N HCl in EtOAc (5.4 mL). The mixture was stirred at room temperature for 30 minutes. The solid was collected by filtration, washed with ethanol (20 mL) to give the title compound as a white solid (304 mg, 95.2%)

$^1$H NMR (400 MHz, DMSO-$d_6$) δ: 1.27 (s, 6H), 2.71 (s, 3H), 3.40 (s, 3H), 3.98 (s, 2H), 6.92 (d, J=6.4 Hz, 1H), 7.41 (m, 3H), 7.53 (m, 2H), 7.57 (m, 4H), 8.05 (dd, J=2.4 Hz, 1H), 8.46 (d, J=9.2 Hz, 1H), 8.91 (d, J=5.20 Hz, 1H), 11.04 (s, 1H).

Example 6

N-(3-fluoro-4-((7-(2-hydroxy-2-methylpropoxy) quinolin-4-yl)oxy)phenyl)-1,5-dimethyl-3-oxo-2-phenyl-2,3-dihydro-1H-pyrazole-4-carboxamide maleate

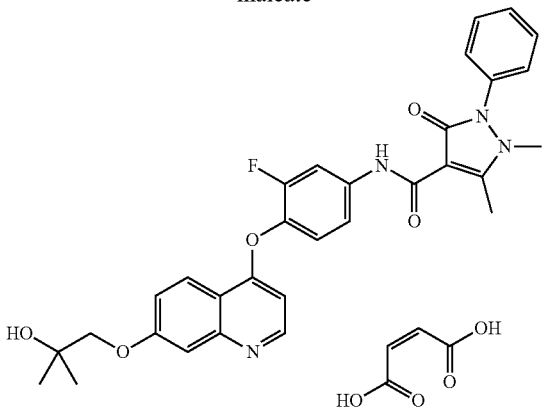

The title compound was prepared according to the procedure described in Example 5 by using N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide (1000 mg, 1.80 mmol) in DCM/MeOH (45 mL, v/v=1:2), and a solution of maleic acid (220 mg, 1.90 mmol) in MeOH (2 mL). The title compound was obtained as a white solid (973 mg, 80.5%).

$^1$H NMR (400 MHz, DMSO-$d_6$): δ 1.26 (s, 6H), 2.71 (s, 3H), 3.92 (s, 2H), 6.20 (s, 1H), 6.58 (d, 5.2 Hz, 1H), 7.32 (m, 2H), 7.35 (m, 2H), 7.41 (m, 4H), 7.50 (m, 1H), 7.58 (m, 2H), 7.99 (d, J=12.8 Hz, 1H), 8.28 (d, J=8.4 Hz, 1H), 8.68 (d, J=4.80 Hz, 1H), 10.99 (s, 1H).

Example 7

N-(3-fluoro-4-((7-(2-hydroxy-2-methylpropoxy) quinolin-4-yl)oxy)phenyl)-1,5-dimethyl-3-oxo-2-phenyl-2,3-dihydro-1H-pyrazole-4-carboxamide p-toluenesulfonate

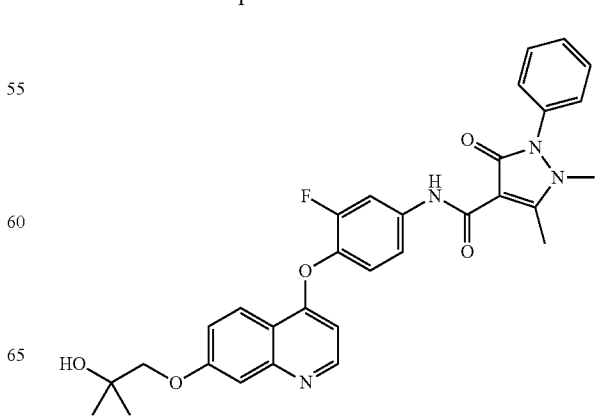

-continued

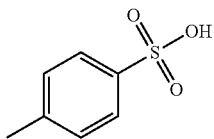

The title compound was prepared according to the procedure described in Example 5 by using N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide (1.0 g, 1.80 mmol) in DCM/MeOH (45 mL, v/v=1:2), and a solution of p-toluenesulfonic acid (325 mg, 1.89 mmol) in MeOH (2 mL). The title compound was obtained as a white solid (910 mg, 70%).

$^1$H NMR (400 MHz, DMSO-$d_6$): δ 1.39 (s, 6H), 2.35 (s, 3H), 2.80 (s, 3H), 3.39 (s, 3H), 4.14 (s, 2H), 6.68 (d, 6.4 Hz, 1H), 7.18 (m, 3H), 7.35 (m, 3H), 7.45 (m, 2H), 7.55 (m, 2H), 7.86 (d, J=8.0 Hz, 2H), 8.00 (dd, J=2.4 Hz, 1H), 8.07 (d, J=2.0 Hz, 1H), 8.38 (d, J=9.2 Hz, 1H), 8.69 (d, J=6.80 Hz, 1H), 11.01 (s, 1H).

Example 8

N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide benzenesulfonate

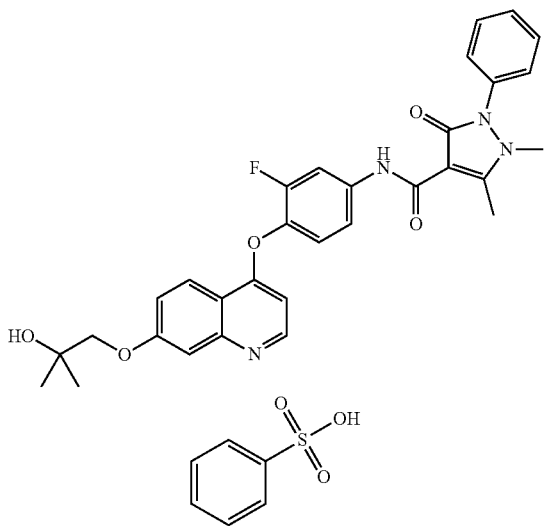

The title compound was prepared according to the procedure described in Example of 5 by using N-(3-fluoro-4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide (650 mg, 1.17 mmol) in DCM/MeOH (30 mL, v/v=1:2), and a solution of benzenesulfonic acid (194 mg, 1.22 mmol) in MeOH (1.5 mL). The title compound was obtained as a white solid (595 mg, 71.5%).

$^1$H NMR (400 MHz, DMSO-$d_6$): δ 1.27 (s, 6H), 2.71 (s, 3H), 3.98 (s, 2H), 6.94 (d, J=6.4 Hz, 1H), 7.41 (m, 3H), 7.51 (m, 2H), 7.55 (m, 1H), 7.57 (m, 5H), 8.05 (dd, J=2.0 Hz, 1H), 8.47 (d, J=9.2 Hz, 1H), 8.93 (d, J=6.80 Hz, 1H), 11.05 (s, 1H).

Example 9

N-(4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide

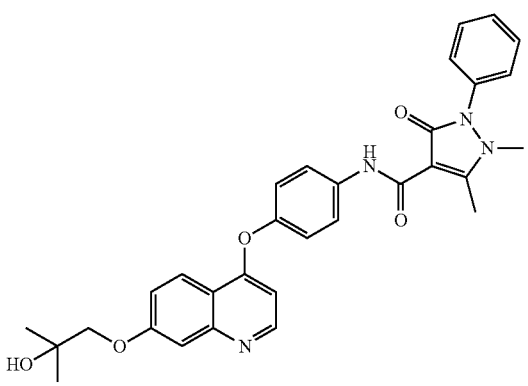 [SMILES: Cc1c(C(=O)Nc2ccc(Oc3ccnc4cc(OCC(C)(C)O)ccc34)cc2)c(=O)n(-c2ccccc2)n1C]

Step 1) 7-(benzyloxy)-4-(4-nitrophenoxy)quinoline

To a suspension of 7-(benzyloxy)-4-chloroquinoline (10 g, 37.1 mmol) and 4-nitrophenol (6.2 g, 44.5 mmol) in toluene (10 mL) was added DIPEA (6.2 g, 48.2 mmol). The reaction mixture was refluxed at 115° C. for 12 hours, then cooled down to room temperature. DCM (50 mL) was added to the mixture, and the resulted solution was washed with 1 M NaOH (30 mL each) several times till the water phase was colorless. The organic phase was concentrated in vacuo to afford a brown solid (13.2 g, 95.7%). The solid was stirred in 95% EtOH (30 mL) at room temperature for 12 hours, and filtered to give the title compound as a gray-brown solid (12.1 g, 91.7%).

MS (ESI, pos. ion) m/z: 373.1 [M+1];

$^1$H NMR (400 MHz, DMSO-$d_6$): δ 5.32 (s, 2H), 6.86-6.88 (d, J=8.0 Hz, 1H), 7.35-7.36 (t, 1H), 7.38-7.40 (m, 1H), 7.42-7.44 (m, 2H), 7.52-7.54 (d, J=8.0 Hz, 2H), 7.56-7.57 (d, J=4.0 Hz, 1H), 8.06-8.08 (d, J=8.0 Hz, 1H), 8.32-8.34 (m, 2H), 8.74-8.75 (d, J=4.0 Hz, 1H).

Step 2) 4-(4-nitrophenoxy)quinolin-7-ol

To a mixture of 7-(benzyloxy)-4-(4-nitrophenoxy)quinoline (10.85 g, 29.14 mmol) and 1,4-dioxane (38 mL) was added concentrated hydrochloric acid (38 mL). The reaction was stirred in an oil bath at 100° C. for 9 hours, monitored by TLC and LC-MS. After the complete consumption of 7-(benzyloxy)-4-(4-nitrophenoxy)quinoline, the mixture was cooled to room temperature. The solid was collected and stirred in 95% EtOH (30 mL) for 2 hours. The title compound was collected by filtration as a beige solid (8.25 g, 88.7%).

MS (ESI, pos. ion) m/z: 283.1 [M+1];

$^1$H NMR (400 MHz, DMSO-$d_6$): δ 6.94-6.96 (d, J=6.6 Hz, 1H), 7.51-7.53 (dd, J=2.24 Hz, J=2.24 Hz, 1H), 7.70-7.75 (m, 3H), 8.41-8.48 (m, 3H), 8.92-8.94 (d, J=6.6 Hz, 1H), 11.93 (s, 1H).

Step 3) 2-methyl-1-((4-(4-nitrophenoxy)quinolin-7-yl)oxy)propan-2-ol

To a flask containing 4-(4-nitrophenoxy)quinolin-7-ol (14.45 g, 45.33 mmol) was added a solution of sodium hydroxide (3.63 g, 90.66 mmol) in water/95% EtOH (90 mL/10 mL) followed by isobutylene oxide (12.12 mL, 136 mmol, pre-cooled to 0° C.). After stirring at 45° C. for 10 minutes, more isobutylene oxide (12.12 mL, 136 mmol, pre-cooled to 0° C.) was added. The reaction was continued to stir for additional 12 hours. The mixture was cooled to room temperature and continued to stir for 4 hours, then cooled to 0° C. and stirred for additional 10 minutes. The resulted solid was filtered, and then dissolved in DCM (130 mL). The solution was filtered and concentrated in vacuo. The residue was washed with petroleum ether (30 mL), and dried in vacuo at 45° C. overnight to afford the title compound as a yellow solid (6.86 g, 42.7%).

Step 4) 1-((4-(4-aminophenoxy)quinolin-7-yl)oxy)-2-methylpropan-2-ol

To a solution of 2-methyl-1-((4-(4-nitrophenoxy)quinolin-7-yl)oxy)propan-2-ol (2.8 g, 7.9 mmol) and HCOOK (4.6 g, 55.3 mmol) in water (4 mL) and THF (12 mL) was added 10% Pd/C (0.24 g). The reaction mixture was stirred at 45° C. for 21 hours and then cooled to room temperature. The mixture was filtered through a Celite pad. The organic phase was separated and washed with brine (20 mL). The aqueous phase was extracted with EtOAc (15 mL). The combined organic phases were concentrated in vacuo and the residue was dried in vacuo at 50° C. overnight to give the title compound as a yellow solid (2.5 g, 97.7%).

MS (ESI, pos. ion) m/z: 325.2 [M+1];
$^1$H NMR (400 MHz, DMSO-$d_6$): δ 1.27 (s, 6H), 3.16-3.17 (d, J=4.0 Hz, 1H), 3.89 (s, 2H), 4.73 (s, 1H), 5.15 (s, 2H), 6.36-6.37 (d, J=4.0 Hz, 1H), 6.66-6.68 (m, 2H), 6.91-6.93 (m, 2H), 7.26-7.29 (dd, J=2.52 Hz, J=2.48 Hz, 1H), 8.74-8.75 (d, J=4.0 Hz, 1H).

Step 5) N-(4-((7-(2-hydroxy-2-methylpropoxy)quinolin-4-yl)oxy)phenyl)-1,5-dimethyl-3-oxo-2-phenyl-2,3-dihydro-1H-pyrazole-4-carboxamide To a solution of 1-((4-(4-aminophenoxy)quinolin-7-yl)oxy)-2-methylpropan-2-ol (3.75 g, 11.6 mmol) in DCM (31 mL) was added 1,5-dimethyl-3-oxo-2-phenyl-2,3-dihydro-1H-pyrazole-4-carboxylic acid (2.7 g, 11.8 mmol), HOAT (0.32 g, 2.32 mmol), EDCI (2.7 g, 13.9 mmol). The reaction mixture was refluxed for 3 hours, then cooled to 45° C. and continued to stir for 4 hours. Additional EDCI (0.4 eq., 0.90 g, 4.64 mmol) was added and the reaction was stirred overnight at 45° C. The mixture was cooled to room temperature and diluted with a mixture of EtOAc (30 mL) and water (30 mL). After stirring at room temperature for 2 hours, the mixture was filtered. The solid was stirred in 95% EtOH (15 mL) at −5° C. for 5 hours. The solid was collected through filtration, dried in vacuo at 50° C. overnight to give the title compound as a gray-white solid (3.04 g, 48.87%).

MS (ESI, pos. ion) m/z: 539.2 [M+1];
$^1$H NMR (400 MHz, CDCl$_3$): δ 1.40 (s, 6H), 2.80 (s, 3H), 3.36 (s, 3H), 3.97 (s, 2H), 6.45-6.46 (d, J=5.2 Hz, 1H), 7.11-7.13 (d, J=8.56 Hz, 2H), 7.36-7.39 (m, 3H), 7.47-7.49 (d, J=6.8 Hz, 1H), 7.54-7.58 (m, 2H), 7.74-7.76 (d, J=8.4 Hz, 2H), 8.25-8.27 (d, J=9.04 Hz, 1H), 8.56-8.57 (d, J=5.08 Hz, 1H).

$^{13}$C NMR (100 MHz, DMSO-$d_6$): δ 11.46, 26.63, 33.31, 48.62, 68.63, 76.24, 97.04, 108.13, 119.04, 120.75, 121.56, 122.81, 127.19, 128.91, 129.51, 133.02, 136.46, 148.93, 151.82, 153.75, 160.37, 161.18, 161.24, 163.05.

Example 10

N-(4-((7-(2-hydroxyethoxy)quinolin-4-yl)oxy)phenyl)-1,5-dimethyl-3-oxo-2-phenyl-2,3-dihydro-1H-pyrazole-4-carboxamide

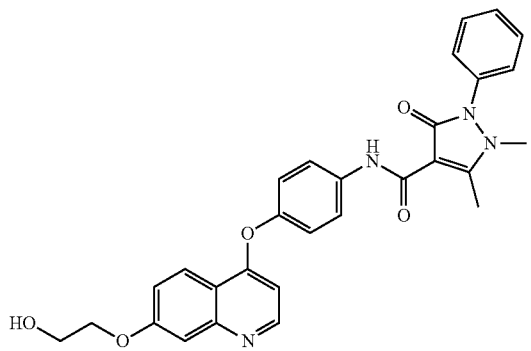 [SMILES: Cc1c(C(=O)Nc2ccc(Oc3ccnc4cc(OCCO)ccc34)cc2)c(=O)n(-c2ccccc2)n1C]

Step 1) 2-((4-(4-nitrophenoxy)quinolin-7-yl)oxy)ethanol

To a solution of 4-(4-nitrophenoxy)quinolin-7-ol (2.82 g, 10 mmol) in DMF (20 mL) was added KOH pellets (1.12 g, 20 mmol) and 2-bromoethanol (1.87 g, 15 mmol) at room temperature. The reaction was then warmed up to 45° C. and stirred for 12 hours. The mixture was then concentrated in vacuo and the residue was purified by a column chromatography on silica gel (EtOAc/PE=1:1) to give the title compound as a pale yellow solid (417 mg, 12.8%).

MS (ESI, pos. ion) m/z: 327.1 [M+1].
$^1$H NMR (400 MHz, DMSO-$d_6$): δ 8.74 (d, J=5.1 Hz, 1H), 8.34 (dd, J$_1$=2.2 Hz, J$_2$=7.0 Hz, 2H), 8.06 (d, J=9.2 Hz, 1H), 7.45 (m, 3H), 7.31 (dd, J$_1$=2.5 Hz, J$_2$=9.2 Hz, 1H), 4.97 (t, J=5.5 Hz, 1H), 4.18 (t, J$_1$=4.7 Hz, J$_2$=5.0 Hz, 2H), 3.80 (m, 2H).

Step 2) 2-((4-(4-aminophenoxy)quinolin-7-yl)oxy)ethanol

To a suspension of 2-((4-(4-nitrophenoxy)quinolin-7-yl)oxy)ethanol (0.32 g, 1 mmol), HCOOK (0.59 g, 7 mmol) in water (1 mL) and THF (3 mL) was added 10% Pd/C (0.03 g). The reaction was stirred at 45° C. for 4 hours. The mixture was diluted with EtOAc (5 mL), filtered through a Celite pad. The filtrate was concentrated in vacuo, washed with a mixture of 95% ethanol (1 mL) and water (5 mL). The solid was collected by filtration and dried in vacuo at 50° C. overnight to give the title compound as a pale yellow solid (140 mg, 47.3%).

MS (ESI, pos. ion) m/z: 297.2 [M+1].
$^1$H NMR (400 MHz, DMSO-$d_6$): δ 8.54 (d, J=5.2 Hz, 1H), 8.19 (d, J=9.1 Hz, 1H), 7.36 (d, J=2.5 Hz, 1H), 7.26 (dd, J$_1$=2.5 Hz, J$_2$=9.1 Hz, 1H), 6.92 (dd, J$_1$=2.1 Hz, J$_2$=6.7 Hz, 2H), 6.66 (dd, J$_1$=2.2 Hz, J$_2$=6.7 Hz, 2H), 6.36 (d, J=5.3 Hz, 1H), 5.16 (s, 2H), 4.96 (s, 1H), 4.16 (t, J$_1$=4.7 Hz, J$_2$=5.0 Hz, 2H), 3.80 (t, J=4.6 Hz, 2H).

Step 3) N-(4-((7-(2-hydroxyethoxy)quinolin-4-yl)oxy)phenyl)-1,5-dimethyl-3-oxo-2-phenyl-2,3-dihydro-1H-pyrazole-4-carboxamide To a solution of 2-((4-(4-aminophenoxy)quinolin-7-yl)oxy)ethanol (0.14 g, 0.5 mmol), 1,5-dimethyl-3-oxo-2-phenyl-2,3-dihydro-1H-pyrazole-4-carboxylic acid (0.11 g, 0.51 mmol) in DCM (1.5 mL) was added HOAT (0.014 g, 0.1 mmol), and EDCI (0.11 g, 0.6 mmol). The reaction was refluxed for 3 hours. The cooled mixture was diluted with water (30 mL) and filtered. The solid was collected and stirred in a mixture of EtOAc (3 mL) and water (3 mL) overnight. The solid was collected by filtration and dried in vacuo at 50° C. for 9 hours to afford the title compound as a gray-white solid (180 mg, 74.7%).

MS (ESI, pos. ion) m/z: 511.3 [M+1].

$^1$H NMR (400 MHz, DMSO-$d_6$): δ 10.83 (s, 1H), 8.59 (d, J=5.1 Hz, 1H), 8.20 (d, J=9.2 Hz, 1H), 7.73 (d, J=8.8 Hz, 2H), 7.59 (t, J=7.6 Hz, 2H), 7.52 (m, 1H), 7.43 (d, J=7.5 Hz, 2H), 7.39 (s, 1H), 7.29 (d, J=8.9 Hz, 1H), 7.24 (d, J=8.8 Hz, 1H), 6.47 (d, J=5.2 Hz, 1H), 4.95 (t, J=5.4 Hz, 1H), 4.17 (t, J=4.4 Hz, 2H), 3.80 (d, J=4.4 Hz, 2H), 3.34 (s, 3H), 2.71 (s, 3H).

Example 11

(R)—N-(4-((7-(2-hydroxypropoxy)quinolin-4-yl)oxy)phenyl)-1,5-dimethyl-3-oxo-2-phenyl-2,3-dihydro-1H-pyrazole-4-carboxamide

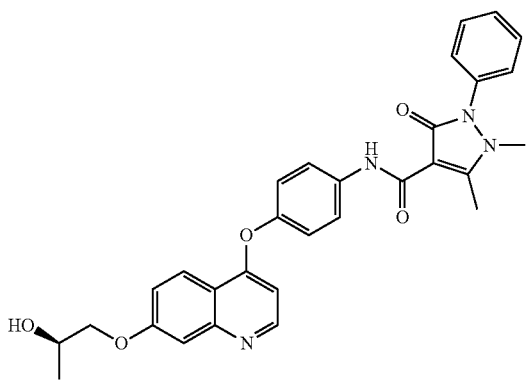 [SMILES: Cc1c(C(=O)Nc2ccc(Oc3ccnc4cc(OC[C@@H](C)O)ccc34)cc2)c(=O)n(-c2ccccc2)n1C]

Step 1) (R)-1-((4-(4-nitrophenoxy)quinolin-7-yl)oxy)propan-2-ol

To a suspension of 4-(4-nitrophenoxy)quinolin-7-ol (10 g, 35.5 mmol) in THF (35 mL)/aq. NaOH (37.8 g, 7.4%) was added (R)-2-methyloxirane (10.3 g, 177.3 mmol). The reaction was stirred at 30° C. for 18 hours then concentrated in vacuo. The mixture was diluted with EtOAc (50 mL). The organic phase was separated and concentrated in vacuo. The residue was purified by a column chromatography on silica gel (EtOAc/PE=1:1) to furnish the title compound as a yellow solid (3.6 g, 29.9%).

MS (ESI, pos. ion) m/z: 341.10 [M+1];

Step 2) (R)-1-((4-(4-aminophenoxy)quinolin-7-yl)oxy)propan-2-ol

To a suspension of (R)-1-((4-(4-nitrophenoxy)quinolin-7-yl)oxy)propan-2-ol (3.6 g, 10.6 mmol) and HCOOK (6.2 g, 74.1 mmol) in THF/H$_2$O (33 mL/11 mL) was added a catalytic amount of 10% Pd/C (33 mg). After stirring at 73° C. for 5 hours, the reaction mixture was cooled to room temperature. The mixture was filtered through a celite pad and the filter cake was washed with DCM (50 mL). The organic phase was separated, dried over Na$_2$SO$_4$, and concentrated in vacuo. The residue was purified by a column chromatography on silica gel (EtOAc/PE=1:1) to give the title compound as a yellow solid (2.5 g, 76.2%).

MS (ESI, pos. ion) m/z: 311.2 [M+1];

$^1$H NMR (400 MHz, CDCl$_3$): δ 1.32 (d, J=6.4 Hz, 3H), 4.00-4.04 (m, 2H), 4.18-4.20 (m, 1H), 6.42 (d, J=5.44 Hz, 1H), 6.80-6.82 (m, 2H), 6.92-6.94 (m, 2H), 7.26-7.31 (m, 2H), 8.24 (d, J=9.04 Hz, 1H), 8.45 (d, J=5.44 Hz, 1H).

Step 3) (R)—N-(4-((7-(2-hydroxypropoxy)quinolin-4-yl)oxy)phenyl)-1,5-dimethyl-3-oxo-2-phenyl-2,3-dihydro-1H-pyrazole-4-carboxamide To a solution of (R)-1-((4-(4-aminophenoxy)quinolin-7-yl)oxy)propan-2-ol (2.5 g, 11.9 mmol), 1,5-dimethyl-3-oxo-2-phenyl-2,3-dihydro-1H-pyrazole-4-carboxylic acid (2.0 g, 8.6 mmol) and HOAT (0.2 g, 1.6 mmol) in DCM (35 mL) was added EDCI (1.9 g, 9.7 mmol). The reaction mixture was stirred at 43° C. for 12 hours, then cooled to room temperature and diluted with a mixture of DCM and H$_2$O (50 mL/50 mL). The organic phase was separated, dried over Na$_2$SO$_4$ and concentrated in vacuo. The residue was purified by a column chromatography on silica gel (EtOAc) to afford the title compound as a yellow solid (0.6 g, 14.3%).

MS (ESI, pos. ion) m/z: 525.20 [M+1];

$^1$H NMR (400 MHz, CDCl$_3$): δ 1.34 (d, J=6.4 Hz, 3H), 2.80 (s, 3H), 3.36 (s, 3H), 3.96-4.13 (m, 2H), 4.29-4.30 (m, 1H), 6.45 (d, J=5.28 Hz, 1H), 7.11-7.13 (m, 2H), 7.21-7.24 (m, 1H), 7.35-7.39 (m, 3H), 7.45-7.49 (m, 1H), 7.54-7.57 (m, 2H), 7.74-7.76 (m, 2H), 8.25 (d, J=9.16 Hz, 1H), 8.56 (d, J=5.28 Hz, 1H).

Example 12

(S)—N-(4-((7-(2-hydroxypropoxy)quinolin-4-yl)oxy)phenyl)-1,5-dimethyl-3-oxo-2-phenyl-2,3-dihydro-1H-pyrazole-4-carboxamide

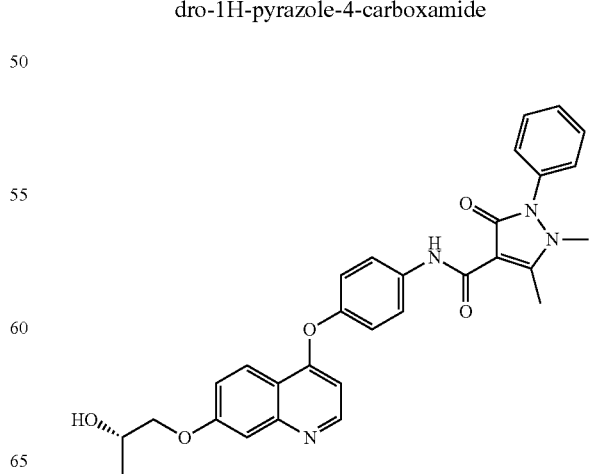

The title compound was prepared according to the procedure described in Example 11 by using (S)-1-((4-(4-aminophenoxy)quinolin-7-yl)oxy)propan-2-ol (3.24 g, 10.5 mmol), 1,5-dimethyl-3-oxo-2-phenyl-2,3-dihydro-1H-pyrazole-4-carboxylic acid (2.55 g, 11.0 mmol), EDCI (2.4 g, 12.5 mmol) and HOAT (0.28 g, 2.1 mmol) in DCM (21 mL). The crude product was purified by a column chromatography on silica gel (EtOAc) to afford the title compound as a yellow solid (1.82 g, 33.2%).

MS (ESI, pos. ion) m/z: 525.20 [M+1];

$^1$H NMR (400 MHz, CDCl$_3$): δ 1.34 (d, J=6.4 Hz, 3H), 2.81 (s, 3H), 3.35 (s, 3H), 3.95-4.13 (m, 2H), 4.28-4.29 (m, 1H), 6.44 (d, J=5.28 Hz, 1H), 7.11-7.13 (m, 2H), 7.22-7.24 (m, 1H), 7.35-7.39 (m, 3H), 7.46-7.49 (m, 1H), 7.55-7.58 (m, 2H), 7.74-7.76 (m, 2H), 8.26 (d, J=9.16 Hz, 1H), 8.56 (d, J=5.28 Hz, 1H).

Example 13

N-(3-fluoro-4-((7-(2-hydroxyethoxy)quinolin-4-yl)oxy)phenyl)-1,5-dimethyl-3-oxo-2-phenyl-2,3-dihydro-1H-pyrazole-4-carboxamide

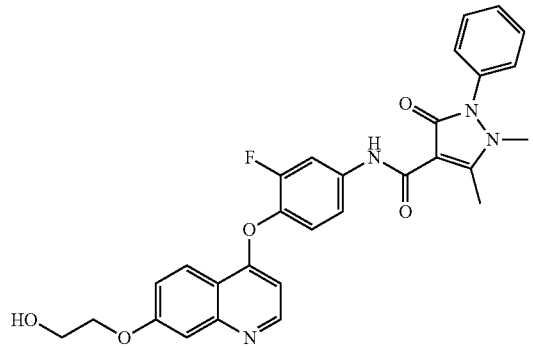

Chemical Formula: C$_{29}$H$_{25}$FN$_4$O$_5$
Exact Mass: 528.18

The title compound was prepared according to the procedure described in Example 10 by using 2-((4-(4-amino-2-fluorophenoxy)quinolin-7-yl)oxy)ethanol (90 mg, 0.28 mmol), 1,5-dimethyl-3-oxo-2-phenyl-2,3-dihydeo-1H-pyrazole-4-carboxylic acid (67.8 mg, 0.29 mmol), EDCI (65.9 mg, 0.34 mmol) and HOAT (8 mg, 0.06 mmol) in DCM (3 mL). The crude product was purified by a column chromatography on silica gel (PE:EtOAc=1:1 to EtOAc) to afford the title compound as a light yellow solid (70 mg, 46.3%).

LC-MS (ESI, pos. ion) m/z: 529 [M+1], Rt=3.062 min;

$^1$H NMR (400 MHz, DMSO-d$_6$): δ 2.71 (s, 3H), 3.32 (s, 3H), 3.78-3.82 (dd, J=5.32 Hz, J=9.92 Hz, 2H), 4.16-4.19 (t, J=5.04 Hz, J=9.76 Hz, 2H), 4.94-4.96 (t, J=5.48 Hz, J=11.04 Hz, 1H), 6.47-6.48 (dd, J=0.84 Hz, J=5.24 Hz, 1H) 7.30-7.36 (m, 2H), 7.40-7.45 (m, 4H), 7.52-7.54 (m, 1H), 7.53-7.61 (m, 2H), 7.96-8.00 (dd, J=2.4 Hz, 13.08 Hz, 1H), 8.22 (d, J=9.16 Hz, 1H), 8.60 (d, J=5.2 Hz, 1H), 10.97 (s, 1H).

Example 14

N-(3-fluoro-4-((7-((1-hydroxy-2-methylpropan-2-yl)oxy)quinolin-4-yl)oxy)phenyl)-1,5-dimethyl-3-oxo-2-phenyl-2,3-dihydro-1H-pyrazole-4-carboxamide

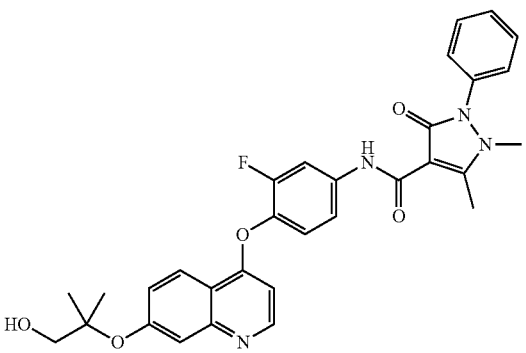 [SMILES: Cc1c(C(=O)Nc2ccc(Oc3ccnc4cc(OC(C)(C)CO)ccc34)c(F)c2)c(=O)n(-c2ccccc2)n1C]

Step 1) 2-((4-(2-fluoro-4-nitrophenoxy)quinolin-7-yl)oxy)-2-methylpropanoic acid To a mixture of 4-(2-fluoro-4-nitrophenoxy)quinolin-7-ol (5 g, 16.7 mmol) and NaOH (6.7 g, 166.7 mmol) in acetone (67 mL) was added chloroform (21.9 g, 183.3 mmol) dropwise at room temperature. After the mixture turned brown color, the reaction was heated to reflux for 1 hour. Water (10 mL) was then added to the reaction mixture, and the resulted solution was adjusted to pH 3~4 with 1 N HCl solution. The resulted mixture was concentrated in vacuo, and then extracted with EtOAc (30 mL). The organic phase was separated, concentrated in vacuo, and treated with 95% EtOH (10 mL). The resulted solid was collected by filtration, dried in vacuo overnight to afford the title compound as a brown solid (2.34 g, 36.4%).

LC-MS (ESI, pos, ion) m/z: 387 [M+1];

$^1$H NMR (400 MHz, CDCl$_3$): δ 1.92 (s, 6H), 6.48-6.49 (m, 1H), 7.27-7.40 (m, 2H), 7.82 (d, 1H, J=2.44 Hz), 8.13-8.19 (m, 3H), 8.54 (d, J=5.6 Hz, 1H).

Step 2) methyl 2-((4-(2-fluoro-4-nitrophenoxy)quinolin-7-yl)oxy)-2-methylpropanoate To a solution of 2-((4-(2-fluoro-4-nitrophenoxy)quinolin-7-yl)oxy)-2-methylpropanoic acid (3 g, 7.75 mmol), EDCI (1.8 g, 9.3 mmol) and HOAT (0.2 g, 1.6 mmol) in CH$_2$Cl$_2$ (60 mL) was added CH$_3$OH (5 mL). The reaction mixture was stirred at room temperature for 1 hour and then diluted with 20 mL of CH$_2$Cl$_2$. The organic phase was separated, washed with water (20 mL) and concentrated in vacuo. The crude product was purified by a column chromatography on silica gel (PE/EtOAc=2:1) to afford the title compound as a yellow oil (3 g, 96.5%).

Step 3) 2-((4-(2-fluoro-4-nitrophenoxy)quinolin-7-yl)oxy)-2-methylpropan-1-ol To a solution of methyl 2-((4-(2-fluoro-4-nitrophenoxy)quinolin-7-yl)oxy)-2-methylpropanoate (3 g, 7.5 mmol) in THF (25 mL) was added LiAlH$_4$ (0.34 g, 9 mmol) in portions at 0° C. The reaction was stirred at 0° C. for 4 hours and then quenched with H$_2$O (30 mL). The organic solvent was removed in vacuo and the residue was diluted with DCM (100 mL). The organic phase was separated, dried over Na$_2$SO$_4$ and concentrated in vacuo. The title compound was obtained as a yellow solid (0.95 g, 34.1%).

MS (ESI, pos, ion) m/z: 373 [M+1];

$^1$H NMR (400 MHz, CDCl$_3$): δ 1.47 (s, 6H), 3.72 (s, 2H), 6.55-6.56 (m, 1H), 7.27-7.38 (m, 2H), 7.72 (d, J=2.28 Hz, 1H), 8.13-8.19 (m, 3H), 8.71 (d, J=5.12 Hz, 1H).

Step 4) 2-((4-(4-amino-2-fluorophenoxy)quinolin-7-yl)oxy)-2-methylpropan-1-ol To a solution of 2-((4-(2-fluoro-4-nitrophenoxy)quinolin-7-yl)oxy)-2-methylpropan-1-ol (5.8 g, 15.6 mmol) in THF (23 mL) was added a solution of HCOOK (9.16 g, 10.9 mmol) in water (7.8 mL), followed by a catalytic amount of Pd/C (5%, 53%~55% water content). The mixture was heated to 45° C. and stirred for 12 hours, and then filtered through a celite pad. The organic phase was separated, dried over Na$_2$SO$_4$ and concentrated in vacuo to afford a yellow foam solid. The title compound was purified by a silica gel chromatography (EtOAc/DCM=1/1) to give a light yellow solid (4.0 g, 75%).

MS (ESI, pos. ion) m/z: 343.1 [M+1];

HPLC: Rt: 7.467 min, purity: 99.17% at 254 nm and 99.09% at 210 nm;

$^1$H NMR (400 MHz, DMSO-d$_6$): δ1.33 (s, 6H), 3.49 (s, 2H), 5.05 (s, 1H), 5.49 (d, J=7.0 Hz, 2H), 6.43 (dd, J=1.0 Hz, J=5.18 Hz, 1H), 6.48 (dd, J=1.92 Hz, J=8.0 Hz, 1H), 6.56 (dd, J=2.52 Hz, J=13.16 Hz, 1H), 7.08 (t, J=8.96 Hz, J=18.04 Hz, 1H), 7.34 (dd, J=2.36 Hz, J=9.0 Hz, 1H), 7.56 (d, J=2.28 Hz, 1H), 8.21 (d, J=9.08 Hz, 1H), 8.60 (d, J=5.2 Hz, 1H).

Step 5) N-(3-fluoro-4-((7-((1-hydroxy-2-methylpropan-2-yl)oxy)quinolin-4-yl)oxy)phenyl)-1,5-dimethyl-3-oxo-2-phenyl-2,3-dihydro-1H-pyrazole-4-carboxamide To a solution of 2-((4-(4-amino-2-fluorophenoxy)quinolin-7-yl)oxy)-2-methylpropan-1-ol (2.84 g, 8.3 mmol) in DCM (30 mL) was added 1,5-dimethyl-3-oxo-2-phenyl-2,3-dihydro-1H-pyrazole-4-carboxylic acid (1.97 g, 8.4 mmol), EDCI (1.92 g, 10.0 mmol) and HOAT (0.23 g, 1.7 mmol). The reaction mixture was stirred at reflux for 4 hours and then concentrated in vacuo. The residue was stirred in 95% EtOH (50 mL)/water (30 mL), and then filtered to give the title compound as a light yellow solid (3.52 g, 76.2%).

MS (ESI, pos. ion) m/z: 557.2 [M+1];

$^1$H NMR (400 MHz, CDCl$_3$): δ 10.88 (s, 1H), 8.62-8.60 (d, J=5.2 Hz, 1H), 8.31-8.28 (d, J=9.0 Hz, 1H), 7.94-7.93 (dd, J=12.4 Hz, 1H), 7.66-7.65 (d, J=2.2 Hz, 1H), 7.58-7.55 (m, 2H), 7.50-7.46 (m, 1H), 7.37-7.35 (d, J=7.4 Hz, 2H), 7.32-7.30 (d, J=8.7 Hz, 1H), 7.26-7.24 (dd, J=12.4 Hz, 1H), 7.19-7.14 (m, 1H), 6.45-6.44 (d, J=5.1 Hz, 1H), 3.69 (s, 2H), 3.37 (s, 3H), 2.80 (s, 3H), 1.44 (s, 6H).

Example 15

N-(4-((7-(2-hydroxy-2-methylpropoxy)-6-methoxyquinolin-4-yl)oxy)phenyl)-1,5-dimethyl-3-oxo-2-phenyl-2,3-dihydro-1H-pyrazole-4-carboxamide

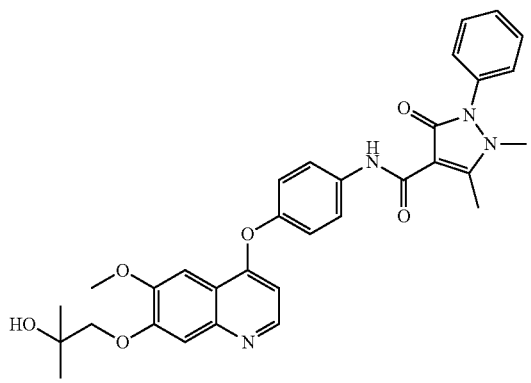 [SMILES: COc1cc2c(Oc3ccc(NC(=O)c4c(C)n(C)n(-c5ccccc5)c4=O)cc3)ccnc2cc1OCC(C)(C)O]

Step 1) 1-(4-Benzyloxy-3-methoxyphenyl)ethanone

A mixture of 4-hydroxy-3-methoxyacetophenone (40 g, 240 mmol), benzyl bromide (34.1 mL, 260 mmol) and potassium carbonate (50.0 g, 360 mmol) in DMF (800 mL) was stirred at 40° C. for 5 hours. The reaction was cooled to room temperature and poured into a mixture of ice and water (2000 mL). The solid was collected by filtration, washed with water and dried in vacuo to give the title compound as a white solid (60.66 g, 98%).

MS (ESI, pos. ion) m/z: 257.2 [M+1].

$^1$H NMR (400 MHz, CDCl$_3$): δ 7.55-7.54 (d, J=2 Hz, 6H), 7.51-7.49 (dd, J=2.04 Hz, J=8.36 Hz, 1H), 7.45-7.43 (m, 2H), 7.40-7.36 (m, 2H), 7.34-7.32 (d, J=7.16 Hz, 1H), 6.90-6.88 (d, J=8.36 Hz, 1H), 5.23 (s, 2H), 3.94 (s, 3H), 2.55 (s, 3H).

Step 2) 1-(4-Benzyloxy-5-methoxy-2-nitrophenyl)ethanone

To a solution of 1-(4-benzyloxy-3-methoxyphenyl)ethanone (51.3 g, 200 mmol) in DCM (750 mL) at 0° C. was added nitric acid (68%, 21 mL, 300 mmol) dropwise over 20 minutes, followed by sulfuric acid (98%, 16.3 mL, 300 mmol) over 40 minutes. Additional nitric acid (14.3 mL, 200 mmol) was added dropwise for another 20 minutes. The reaction mixture was then washed with water until the pH was 7~8, dried over Na$_2$SO$_4$, and concentrated in vacuo. The residue was recrystallized from ethanol (850 mL) to give the title compound as a light yellow solid (40 g, 68%).

MS (ESI, pos. ion) m/z: 302.1 [M+1];

$^1$H NMR (400 MHz, CDCl$_3$): δ 7.66 (s, 1H), 7.46-7.35 (m, 5H), 6.76 (s, 1H), 5.21 (s, 2H), 3.97 (s, 3H), 2.48 (s, 3H).

Step 3) 1-(2-amino-4-(benzyloxy)-5-methoxyphenyl)ethanone

A suspension of 1-(4-Benzyloxy-5-methoxy-2-nitrophenyl)ethanone (36.00 g, 120 mmol), iron powder (26.80 g, 480 mmol) and HCOONH$_4$ (31.53 g, 500 mmol) in a mixture of toluene/water (500 mL/500 mL) was stirred at 103° C. overnight. The mixture was cooled to room temperature, diluted with EtOAc (500 mL), stirred at room temperature for 3 hours, and filtered through a celite pad. The filtrate was concentrated in vacuo to give the title compound as a yellow solid (32.1 g, 99%).

MS (ESI, pos. ion) m/z: 272.2 [M+1];

$^1$H NMR (400 MHz, DMSO-$d_6$): δ 7.46-7.35 (m, 5H), 7.15 (s, 1H), 7.07 (s, 2H), 6.41 (s, 1H), 5.07 (s, 2H), 3.71 (s, 3H), 2.43 (s, 3H).

Step 4) 7-(benzyloxy)-6-methoxyquinolin-4-ol

To a solution of 1-(2-amino-4-(benzyloxy)-5-methoxyphenyl)ethanone (29.00 g, 108 mmol) in DME (700 mL) was added sodium methoxide (46.70 g, 864 mmol) in portions. The reaction was stirred at room temperature for 30 minutes, then ethyl formate was added (64 mL, 648 mmol), and continued to stir for 8 hours. The mixture was diluted with H$_2$O (500 mL) and neutralized with 1 N HCl. The resulted solid was collected through filtration, washed with water and dried in vacuo overnight to afford the title compound as a yellow solid (15.9 g, 53%).

MS (ESI, pos. ion) m/z: 282.2 [M+1];

$^1$H NMR (400 MHz, DMSO-$d_6$): δ 11.58 (s, 1H), 7.77-7.75 (d, J=6.84 Hz, 1H), 7.49-7.36 (m, 6H), 5.95-5.93 (d, J=6.72 Hz, 1H), 5.18 (s, 2H), 3.83 (s, 3H).

Step 5) 7-(benzyloxy)-4-chloro-6-methoxyquinoline

To a solution of 7-(benzyloxy)-6-methoxyquinolin-4-ol (24.60 g, 87.45 mmol) in toluene (75 mL) was added phosphorus oxychloride (90 mL) slowly. The reaction was heated to reflux for 2 hours, and then cooled to room temperature, diluted with EtOAc (200 mL). The resulted solution was poured into a mixture of ice and 3 N NaOH in portions. The pH of the mixture was adjusted with 3 N NaOH to 7~8. The organic phase was separated, washed with water (200 mL) followed by brine (100 mL) and concentration in vacuo. The title compound was obtained as a white solid (22.1 g, 84.5%).

MS (ESI, pos. ion) m/z: 300.01 [M+1];

$^1$H NMR (400 MHz, DMSO-$d_6$): δ 8.60-8.59 (d, J=4.84 Hz, 1H), 7.55-7.54 (m, 6H), 5.95-5.93 (d, J=6.72 Hz, 1H), 5.61 (s, 2H), 3.97 (s, 3H).

Step 6) 7-(benzyloxy)-6-methoxy-4-(4-nitrophenoxy)quinoline

A suspension of 7-(benzyloxy)-4-chloro-6-methoxyquinoline (20.00 g, 70.92 mmol) and p-nitrophenol (13.83 g, 100 mmol) in xylene (40 mL) and N-ethyldiisopropylamine (90 mL) was refluxed for 12 h. The mixture was cooled to rt and diluted with EtOH (200 mL). The solid was collected by filtration and dried in vacuo at 60° C. overnight to give the title compound as a pale yellow solid (22.6 g, 84.3%).

MS (ESI, pos. ion) m/z: 403.1 [M+1];

$^1$H NMR (400 MHz, CDCl$_3$): δ 8.60-8.58 (d, J=5.12 Hz, 1H), 8.33 (s, 2H), 8.31-8.31 (d, J=2.08 Hz, 1H), 7.53-7.50 (d, J=8.04 Hz, 3H), 7.52-7.33 (m, 4H), 7.25-7.24 (d, J=2.08 Hz, 1H), 6.68-6.67 (d, J=5.12 Hz, 1H), 5.33 (s, 2H), 4.00 (s, 3H).

Step 7) 4-(4-aminophenoxy)-6-methoxyquinolin-7-ol

A suspension of 7-(benzyloxy)-6-methoxy-4-(4-nitrophenoxy)quinoline (43.00 g, 120 mmol), 10% Pd/C (4.30 g) and HCOOK (89.93 g, 600 mmol) in MeOH/H$_2$O (345 mL/200 mL) was refluxed overnight. The mixture was cooled to room temperature, diluted with EtOAc (300 mL) and filtered through a celite pad. The filtrate was concentrated in vacuo and the residue was washed with water, dried in vacuo at 60° C. overnight to give the title compound as a yellow solid (28.8 g, 95.5%).

MS (ESI, pos. ion) m/z: 283.1 [M+1];

$^1$H NMR (400 MHz, DMSO-$d_6$): δ 10.03 (s, 1H), 8.36-8.35 (d, J=5.2 Hz, 1H), 7.48 (s, 1H), 7.24 (s, 1H), 6.92-6.90 (dd, J=6.72 Hz, J=2 Hz, 2H), 6.67-6.65 (dd, J=6.68 Hz, J=2.08 Hz, 1H), 6.30-6.28 (d, J=5.24 Hz, 1H), 5.14 (s, 2H), 3.93 (s, 3H).

Step 8) N-(4-((7-hydroxy-6-methoxyquinolin-4-yl)oxy)phenyl)-1,5-dimethyl-3-oxo-2-phenyl-2,3-dihydro-1H-pyrazole-4-carboxamide To a solution of 4-(4-aminophenoxy)-6-methoxyquinolin-7-ol (3.61 g, 12.8 mmol) and 1,5-dimethyl-3-oxo-2-phenyl-2,3-dihydro-1H-pyrazole-4-carboxylic acid (2.85 g, 12.27 mmol) in DMF (50 mL) was added EDCI (2.81 g, 14.66 mmol) and HOAT (0.33 g, 2.4 mmol). The reaction was stirred at 60° C. for 10 hours, cooled to room temperature and diluted with H$_2$O (200 mL). The solid was collected by filtration and dried in vacuo at 60° C. overnight to give the title compound as a white solid (5.7 g, 89.9%).

MS (ESI, pos. ion) m/z: 497.2 [M+1].

$^1$H NMR (400 MHz, DMSO-$d_6$): δ 10.99 (s, 1H), 10.11 (s, 1H), 7.84-7.82 (d, J=8.76 Hz, 2H), 7.78-7.76 (d, J=7.64 Hz, 2H), 7.62-7.58 (t, J=7.84 Hz, 2H), 7.54-7.46 (m, 2H), 7.46-7.43 (m, 4H), 6.42 (s, 1H), 6.03-6.01 (d, J=7.68 Hz, 1H), 3.85 (s, 3H), 3.37 (s, 3H), 2.72 (s, 3H).

Step 9) N-(4-((7-(2-hydroxy-2-methylpropoxy)-6-methoxyquinolin-4-yl)oxy)phenyl)-1,5-dimethyl-3-oxo-2-phenyl-2,3-dihydro-1H-pyrazole-4-carboxamide To a solution of N-(4-((7-hydroxy-6-methoxyquinolin-4-yl)oxy)phenyl)-1,5-dimethyl-3-oxo-2-phenyl-2,3-dihydro-1H-pyrazole-4-carboxamide (4.93 g, 9.93 mmol) and isobutylene oxide (8.8 mL, 100 mmol) in DMF/H$_2$O (21 mL/4 mL) was added K$_2$CO$_3$ (2.74 g, 2 mmol). The reaction mixture was stirred at 60° C. for 12 hours, then cooled to room temperature and treated with aqueous NaH$_2$PO$_4$ (saturated solution, 10 mL) to adjust the pH of the mixture to 7~8. The solid was collected by filtration and washed with EtOAc/EtOH (80 mL/15 mL). The title compound was obtained as a pale yellow solid (1.93 g, 34.3%).

MS (ESI, pos. ion) m/z: 569.2 [M+1].

$^1$H NMR (400 MHz, CDCl$_3$): δ 10.83 (s, 1H), 8.40-8.46 (d, J=5.32 Hz, 1H), 7.77-7.75 (dd, J=2.08 Hz, 6.8 Hz, 2H), 7.58-7.36 (m, 7H), 7.15-7.13 (d, J=8.92 Hz, 2H), 6.49-6.47 (d, J=5.32 Hz, 1H), 4.01 (s, 3H), 3.99 (s, 1H), 3.37 (s, 3H), 2.81 (s, 3H), 1.41 (s, 6H).

Example 16

(S)—N-(4-((7-(2-hydroxypropoxy)-6-methoxyquinolin-4-yl)oxy)phenyl)-1,5-dimethyl-3-oxo-2-phenyl-2,3-dihydro-1H-pyrazole-4-carboxamide

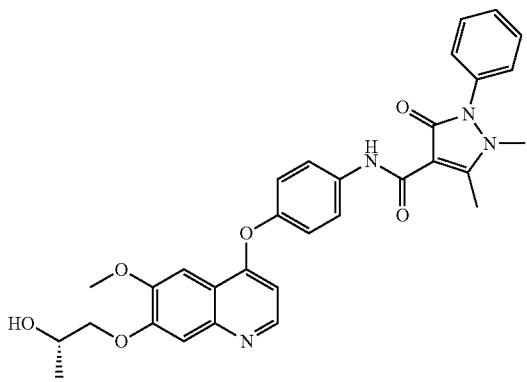

The title compound was prepared according to the procedure described in Example 15 by using N-(4-((7-hydroxy-6-methoxyquinolin-4-yl)oxy)phenyl)-1,5-dimethyl-3-oxo-2-phenyl-2,3-dihydro-1H-pyrazole-4-carboxamide (4.93 g, 9.93 mmol), (S)-2-methyloxirane (8.8 mL, 150 mmol) and $K_2CO_3$ (2.74 g, 19.8 mmol) in DMF/$H_2O$ (21 mL/4 mL). The title compound was purified by a silica gel column chromatography (DCM/MeOH=50/1 to 20/1) and was obtained as a pale solid (2.1 g, 38.3%).

MS (ESI, pos. ion) m/z: 555.2 [M+1].

$^1$H NMR (400 MHz, CDCl$_3$): δ 10.78 (s, 1H), 8.46-8.47 (d, J=5.28 Hz, 1H), 7.74-7.77 (d, J=8.92 Hz, 2H), 7.56-7.58 (m, 3H), 7.47-7.49 (m, 1H), 7.41 (s, 1H), 7.36-7.38 (m, 2H), 7.12-7.14 (d, J=8.88 Hz, 2H), 6.47-6.48 (d, J=5.28 Hz, 1H), 4.32-4.36 (m, 2H), 4.17 (s, 3H), 4.14-4.17 (m, 1H), 3.36 (s, 3H), 2.80 (s, 3H), 1.32-1.34 (d, J=6.4 Hz, 3H).

Example 17

(R)—N-(4-((7-(2-hydroxypropoxy)-6-methoxyquinolin-4-yl)oxy)phenyl)-1,5-dimethyl-3-oxo-2-phenyl-2,3-dihydro-1H-pyrazole-4-carboxamide

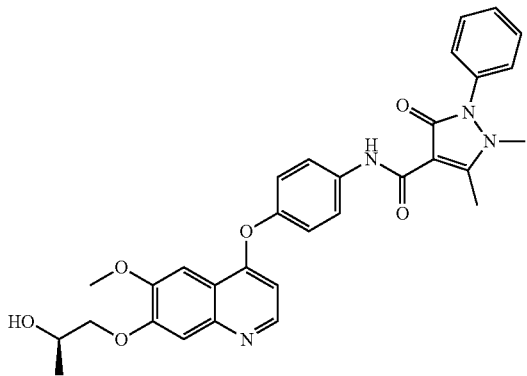 [SMILES: COc1cc2c(Oc3ccc(NC(=O)c4c(C)n(C)n(-c5ccccc5)c4=O)cc3)ccnc2cc1OC[C@H](C)O]

The title compound was prepared according to the procedure described in Example 15 by using N-(4-((7-hydroxy-6-methoxyquinolin-4-yl)oxy)phenyl)-1,5-dimethyl-3-oxo-2-phenyl-2,3-dihydro-1H-pyrazole-4-carboxamide (5.5 g, 11.1 mmol), (R)-2-methyloxirane (8 ml, 111 mmol) and $K_2CO_3$ (3.1 g, 222.2 mmol) in DMF/$H_2O$ (25 mL/5 mL). The crude product was purified by a silica gel column chromatography (DCM/MeOH(V/V=40/1)) to afford the title compound as a gray-white solid (1.5 g, 25%).

MS (ESI, pos. ion) m/z: 555.2 [M+1].

$^1$H NMR (400 MHz, CDCl$_3$): δ 1.32-1.34 (d, J=8 Hz, 3H), 2.80 (s, 3H), 3.36 (s, 3H), 3.96 (s, 3H), 3.99 (m, 1H), 4.33-4.36 (m, 2H), 6.46-6.48 (d, J=5.28 Hz, 1H), 7.12-7.14 (d, J=8.0 Hz, 2H), 7.36-7.40 (m, 3H), 7.47-7.44 (m, 1H), 7.54-7.58 (m, 3H), 7.74-7.77 (m, 2H), 8.46-8.47 (d, J=4 Hz, 1H).

Example 18

N-(4-((7-(2-hydroxyethoxy)-6-methoxyquinolin-4-yl)oxy)phenyl)-1,5-dimethyl-3-oxo-2-phenyl-2,3-dihydro-1H-pyrazole-4-carboxamide

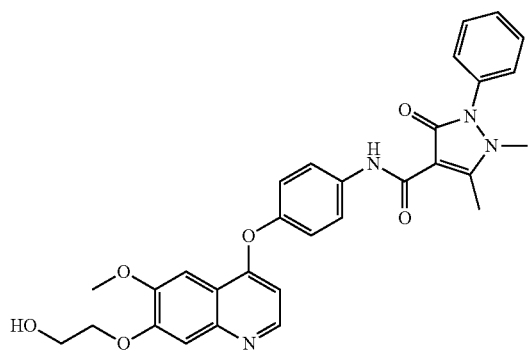 [SMILES: COc1cc2c(Oc3ccc(NC(=O)c4c(C)n(C)n(-c5ccccc5)c4=O)cc3)ccnc2cc1OCCO]

The title compound was prepared according to the procedure described in Example 15 by using N-(4-((7-hydroxy-6-methoxyquinolin-4-yl)oxy)phenyl)-1,5-dimethyl-3-oxo-2-phenyl-2,3-dihydro-1H-pyrazole-4-carboxamide (5 g, 10 mmol), oxirane (5.8 mL, 100 mmol) and $K_2CO_3$ (2.74 g, 2 mmol) in DMF/$H_2O$ (24 mL/6 mL). The crude product was purified by a silica gel column chromatography (DCM/MeOH=30/1) to give the title compound as a pale white solid (0.8 g, 15%).

MS (ESI, pos. ion) m/z: 541.2 [M+1].

$^1$H NMR (400 MHz, CDCl$_3$): δ 10.83 (s, 1H), 8.45-8.46 (d, J=5.24 Hz, 1H), 7.71-7.74 (m, 2H), 7.57-7.61 (m, 2H), 7.49-7.53 (m, 2H), 7.42-7.44 (m, 2H), 7.39 (s, 1H), 7.22-7.24 (d, J=8.92 Hz, 2H), 6.46-6.47 (d, J=5.2 Hz, 1H), 4.16 (t, J=5.0 Hz, 2H), 3.93 (s, 3H), 3.82 (s, 2H), 3.36 (s, 3H), 2.71 (s, 3H).

Biological Testing

The efficacy of the compounds of the invention as inhibitors of receptor tyrosine kinases, such as c-Met, VEGFR and Axl related activity and as anti-tumor agents in xenograft animal models can be evaluated as follows. The assay results demonstrate that certain compounds of the present invention potently inhibit c-Met, VEGF-R2 and Axl phosphorylation in cells, and demonstrate potent, dose dependent anti-tumor activity in certain xenograft models.

Kinase Assays

Kinase assays can be performed by measurement of incorporation of —$^{33}$P ATP into immobilized myelin basic protein (MBP). High binding white 384 well plates (Greiner) are coated with MBP (Sigma #M-1891) by incubation of 60 μl/well of 20 μg/ml MBP in Tris-buffered saline (TBS; 50 mM Tris pH 8.0, 138 mM NaCl, 2.7 mM KCl) for 24 hours at 4° C. Plates are washed 3× with 100 µl TBS. Kinase reactions are carried out in a total volume of 34 µl in kinase buffer (5 mM Hepes pH 7.6, 15 mM NaCl, 0.01% bovine gamma globulin (Sigma #I-5506), 10 mM MgCl$_2$, 1 mM DTT, 0.02% TritonX-100). Compound dilutions are performed in DMSO and added to assay wells to a final DMSO concentration of 1%. Each data point is measured in duplicate, and at least two duplicate assays are performed for each individual compound determination. Enzyme is added to final concentrations of 10 nM or 20 nM, for example. A mixture of unlabeled ATP and —$^{33}$P ATP is added to start the reaction (2×10$^6$ cpm of —$^{33}$P ATP per well (3000 Ci/mmole) and 10 µM unlabeled ATP, typically. The reactions are carried out for 1 hour at room temperature with shaking. Plates are washed 7× with TBS, followed by the addition of 50 µl/well scintillation fluid (Wallac). Plates are read using a Wallac Trilux counter. This is only one format of such assays; various other formats are possible, as known to one skilled in the art.

The above assay procedure can be used to determine the IC$_{50}$ for inhibition and/or the inhibition constant, K$_i$. The IC$_{50}$ is defined as the concentration of compound required to reduce the enzyme activity by 50% under the condition of the assay. The IC$_{50}$ value is estimated by preparing a 10 point curve using a log dilution series (for example, a typical curve may be prepared using the following compound concentrations; 100 µM, 30 µM, 10 µM, 3 µM, 1 µM, 0.3 µM, 0.1 µM, 0.03 µM, 0.01 µM and 30 µM).

The kinase assays described herein were performed at Millipore UK Ltd, Dundee Technology Park, Dundee DD2 1SW, UK c-Met (h) Assay Met (h) is incubated with 8 mM MOPS pH 7.0, 0.2 mM EDTA, 250 µM KKKSPGEYVNIEFG, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting.

KDR (h) (VEGF-R2(h)) Assay

KDR (h) is incubated with 8 mM MOPS pH 7.0, 0.2 mM EDTA, 0.33 mg/mL myelin basic protein, 10 mM MgAcetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting.

Axl (h) Assay

Axl (h) is incubated with 8 mM MOPS pH 7.0, 0.2 mM EDTA, 250 µM KKSRGDYMTMQIG, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 µL of the reaction is then spotted onto a P30 filtermat and washed three times for 5 minutes in 75 mM phosphoric acid and once in methanol prior to drying and scintillation counting.

The compounds disclosed herein exhibited potent activities in the c-Met(h), KDR(h) and Axl(h) assays. Table 2 listed the IC50s of some examples described herein in the c-Met(h), KDR(h) and Axl(h) assays.

TABLE 2

| Example # | IC50 (nM) | | |
|---|---|---|---|
| | c-Met (h) | KDR (h) | Axl (h) |
| Example 1 | 19 | 37 | 11 |
| Example 2 | 7 | 23 | ND |
| Example 4 | 10 | 40 | 17 |
| Example 9 | 13 | ND | 5 |
| Example 11 | 15 | ND | ND |
| Example 12 | 13 | ND | ND |
| Example 14 | 27 | ND | ND |

ND: Not Determined.

Cellular Phosphorylation Assays

Generally, cells are preincubated with test compounds to allow thorough target binding. The autophosphorylation level was determined Sandwich-ELISA technique. IC$_{50}$ values are determined by testing 8 compound concentrations in semi-logarithmic steps (each concentration in duplicates). The steps of the cellular phosphorylation assay are illustrated in FIG. 1. The cellular phosphorylation assays described herein were performed at ProQinase GmbH, Breisacher Straβe 117 D-79106, Freiburg, Germany.

c-Met Phosphorylation Assay:

The human gastric adenocarcinoma cell line MKN45 is known to overexpress c-Met. c-Met overexpression results in a constitutive, ligand-independent autophosphorylation of the kinase. By adding SU11274 phospho-MET levels are largely decreased and thus the dynamic behavior to determine inhibitory potentials of compounds was achieved. Phospho-MET signal is subsequently quantified by Sandwich-ELISA technique. The assay is validated based on known inhibitors of MET kinase activity.

VEGF-R2 Phosphorylation Assay:

Immortalized human umbilical vein endothelial cells (HUE) are known to overexpress human VEGF-R2. Stimulation of these cells with its physiological ligand VEGF-A results in a robust receptor autophosphorylation. Compounds are preincubated before cell stimulation to allow thorough target binding. Stimulation conditions are optimized to determine dose-related inhibition of the phospho-VEGF-R2 signal, which is subsequently quantified by Sandwich-ELISA technique. The assay is validated based on known inhibitors of VEGF-R2 kinase activity.

Axl Phosphorylation Assay:

Cellular AXL phosphorylation assay was generated on a mouse embryonal fibroblast (MEF) background. Cells were transfected to express a full-length AXL protein. After clonal selection a transformed cell line with a high level of autophosphorylated AXL was obtained. By adding Staurosporine phospho-AXL levels are largely decreased and thus the dynamic behavior to determine inhibitory potentials of compounds was achieved. PhosphoAXL levels are quantified by Sandwich-ELISA technique.

The compounds disclosed herein generally exhibited potent activities in c-Met, VEGF-R2 and Axl(h) cellular phosphorylation assays. For example, The IC$_{50}$s of Example 1 was 6.9, 1.7 and <1.0 nM in the c-Met, VEGF-R2 and Axl cellular phosphorylation assays, respectively.

Tumor Xenograft Models

The efficacy of compounds disclosed herein was evaluated in a standard murine model of tumorigenesis. Human tumor cells (U87MG glioblastoma cells, MKN45 Gastric Adenocarcinoma cells, Caki-1 renal carcinoma cells, HUH 7 hepatocarcinoma cells, NCI-H441 lung adenocarcinoma epithelial cells, MDA-MB-231 breast adenocarcinoma cells, SMMC-7721 hepatoma cells, all from ATCC) were expended in culture, harvested, and injected subcutaneously onto the rear flank of 6-7 week old female athymic nude mice (BALB/cA nu/nu, Shanghai SLAC Laboratory Animal, Co.) (n=10 for vehicle group, n=8 for each dosing group). When tumors reached a volume of 100-250 mm³, animals were randomly divided into vehicle control (for example, 2% HPMC+1% Tween-80 in water) and compound groups. Subsequent administration of compound by oral gavage (for example, 3-50 mpk/dose, dissolved in 2% HPMC+1% Tween-80 in water) begins anywhere from day 0 to day 15 post tumor cell challenge and generally continues with once a day for the duration of the experiment. The studies using tumor xenograft animal models described herein were performed at Shanghai Institute of Materia Medica, Chinese Academy of Sciences, 555 Zu Chong Zhi Road, Zhang Jiang Hi-Tech Park, Pudong, Shanghai, 201203, China.

Tumor Growth Inhibition (TGI) Analysis

Progression of tumor growth is assessed by tumor volumes and recorded as a function of time. The long (L) and short (W) axes of the subcutaneous tumors were measured with calipers twice weekly, and the tumor volume (TV) calculated as (L×W²)/2). TGI was calculated from the difference between the median tumor volumes of vehicle-treated and drug-treated mice, expressed as a percentage of the median tumor volume of the vehicle-treated control group, by the following relation:

$$\% \ TGI = \left( \frac{\text{Median Tumor } Volume_{control} - \text{Median Tumor } Volume_{drug-treated}}{\text{Median Tumor } Volume_{control}} \right) \times 100$$

Initial statistical analysis is done by repeated measures analysis of variance (RMANOVA). Followed by Scheffe psot hoc testing for multiple comparisons. Vehicle alone (2% HPMC+1% Tween-80, or the like) is the negative control.

Figure 2:
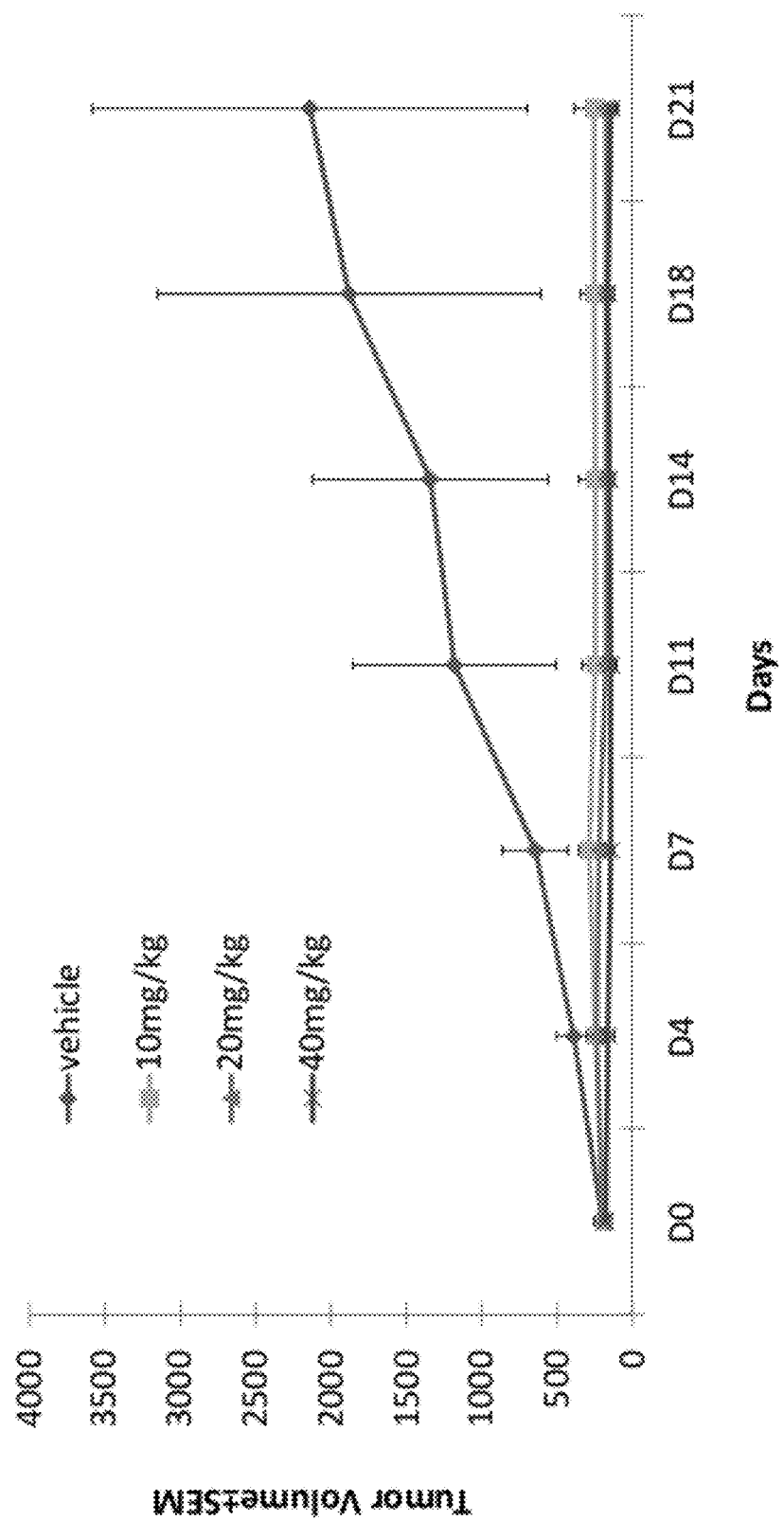
FIG. 2 depicts data showing that Example 1 inhibited the growth of MDA-MB-231 Xenograft tumors in athymic nude mice.

FIG. 2 illustrates the tumor growth inhibition effects of Example 1 in MDA-MB-231 breast adenocarcinoma model. Example 1 was administered orally (p.o.) at doses of 10, 20 and 40 mg/kg once a day (QD), for 21 consecutive days. All doses produced statistically significant, dose-dependent inhibition of growth of MDA-MB-231 tumors grown subcutaneously in athymic nude mice. On the last day of treatment (Day 21), the 10, 20 and 40 mg/kg doses decreased mean tumor volume by 97%, 112%, and 120% (TGI), respectively, compared to the mean tumor volume of the vehicle-treated group.

Figure 3:
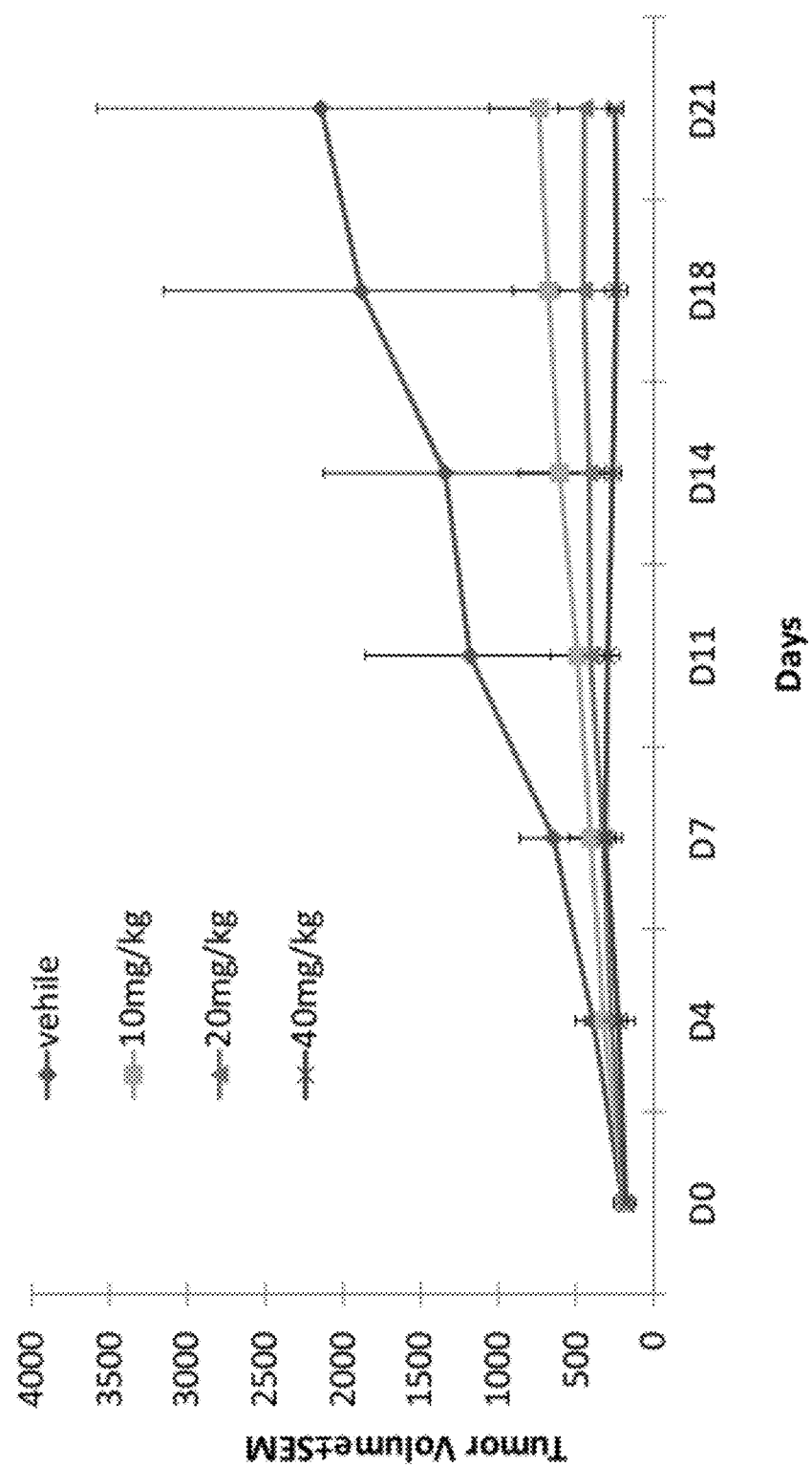
FIG. 3 depicts data showing that Example 2 inhibited the growth of MDA-MB-231 Xenograft tumors in athymic nude mice.

FIG. 3 illustrates the tumor growth inhibition effects of Example 2 in MDA-MB-231 breast adenocarcinoma model. Example 2 was administered orally (p.o.) at doses of 10, 20 and 40 mg/kg once a day (QD), for 21 consecutive days. All doses produced statistically significant, dose-dependent inhibition of growth of MDA-MB-231 tumors grown subcutaneously in athymic nude mice. On the last day of treatment (Day 21), the 10, 20 and 40 mg/kg doses decreased mean tumor volume by 72%, 87%, and 96% (TGI), respectively, compared to the mean tumor volume of the vehicle-treated group.

Example 1 was also administered orally (p.o.) once a day (QD), for 14-21 days in various xenograft animal models. At doses of 20 mg/kg, Example 1 produced statistically significant inhibition of growth of certain tumors grown subcutaneously in athymic nude mice. Exemplary xenograft study results from Examples 1, 2 and 9 are listed in Table 3.

TABLE 3

| TGI % (on last day of dosing) | Xenograft models (dosing schedule, days) | | | | | |
|---|---|---|---|---|---|---|
| | MKN45 (16 days) | Caki-1 (21 days) | NCI-H441 (21 days) | Huh-7 (14 days) | U87MG (16 days) | MDA-MB-231 (21 Days) |
| Example 1 | 97 (20 mpg) | 87 (20 mpg) | 97 (20 mpg) | 53 (20 mpg) | 98 (10 mpg) | 97 (10 mpg) |
| Example 2 | 22 (20 mpg) | ND | ND | ND | ND | 72 (10 mpg) |
| Example 9 | ND | ND | ND | ND | 97 (10 mpg) | ND |

ND: Not Determined; mpg: mg/kg.

Finally, it should be noted that there are alternative ways of implementing the present invention. Accordingly, the present embodiments are to be considered as illustrative and not restrictive, and the invention is not be limited to the details given herein, but may be modified within the scope and equivalents of the appended claims. All publications and patents cited herein are incorporated by reference.

What is claimed is:

1. A compound of Formula (I):

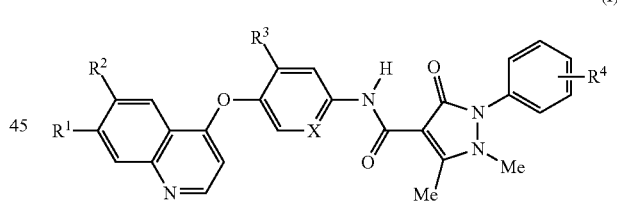

or a stereoisomer, a geometric isomer, a tautomer, an N-oxide, a hydrate, a solvate, a metabolite, a pharmaceutically acceptable salt or a prodrug thereof, wherein:

$R^1$ is hydroxy $C_{2-6}$ alkoxy; $R^2$ is H, alkoxy, or hydroxyalkoxy; $R^3$ is H or F; $R^4$ is H, F, Cl, Br, I, CN, alkyl, haloalkyl, heterocyclyl, heterocyclylalkyl, cycloalkyl, or cycloalkylalkyl; and X is CH or N, wherein at least one of $R^1$ and $R^2$ is hydroxyalkoxy.

2. The compound according to claim 1, wherein $R^3$ is H or F; $R^2$ is H or methoxy; and $R^4$ is H, F, Cl, Br, I, CN, $C_{1-3}$ haloalkyl, $C_{2-5}$ heterocyclyl, $C_{2-5}$ heterocyclyl $C_{1-3}$ alkyl, $C_{3-6}$ cycloalkyl, or $C_{3-6}$ cycloalkyl $C_{1-3}$ alkyl.

3. The compound according to claim 1, wherein $R^2$ is H or methoxy; $R^3$ is H or F; $R^4$ is H or F; and X is CH.

4. The compound according to claim 1, wherein $R^2$ is H; $R^3$ is H or F; $R^4$ is H; and X is CH.

5. The compound of claim 1 having one of the following structures:

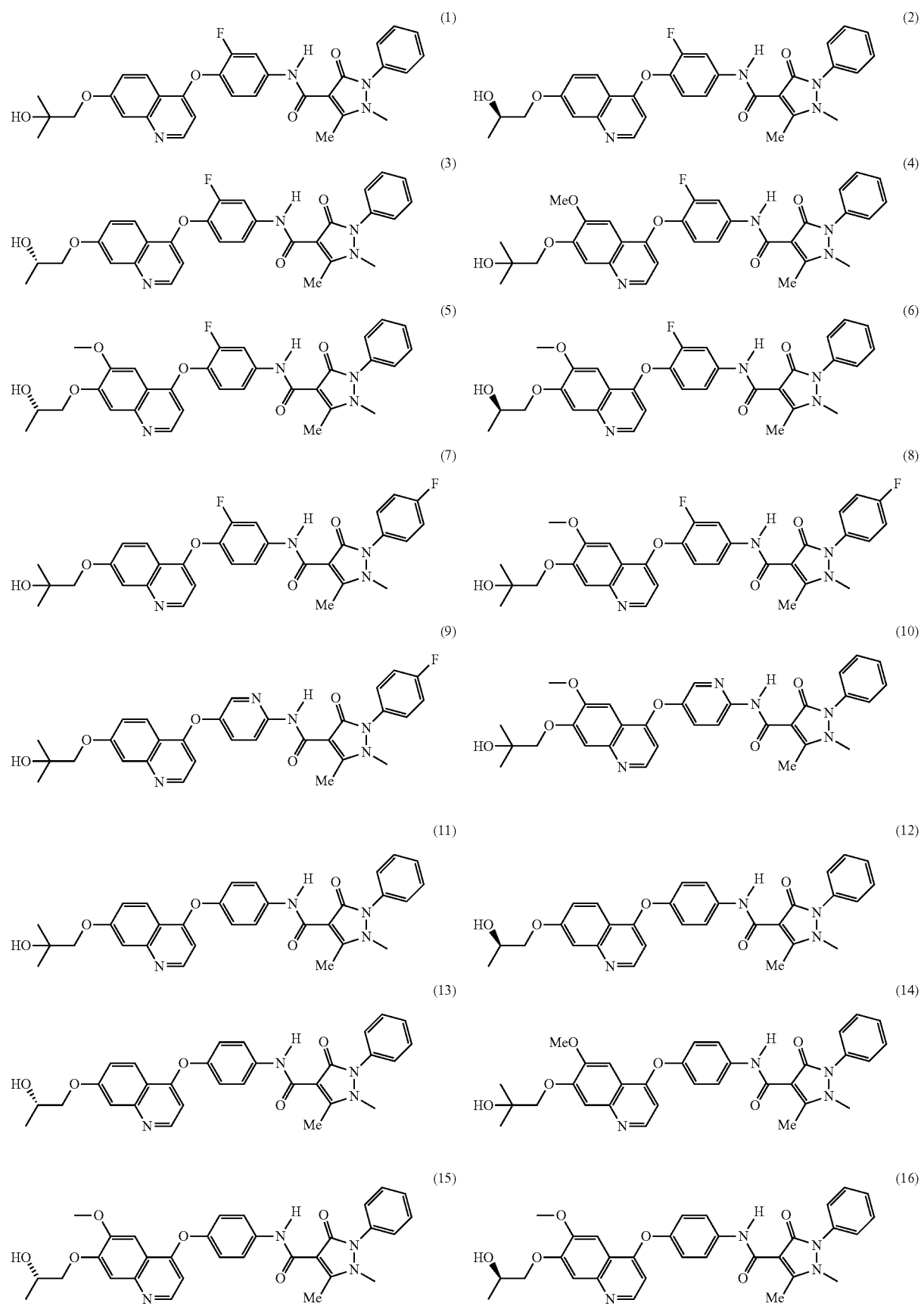

-continued
(17)
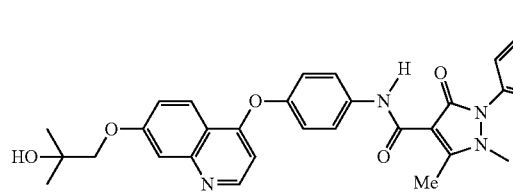
(18)
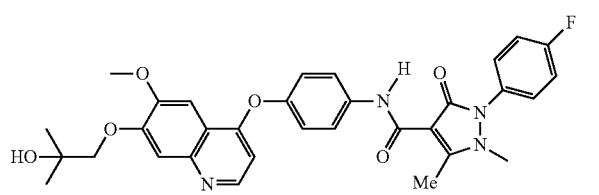
(19)
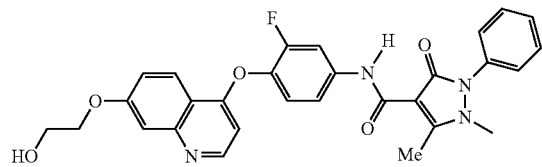
(20)
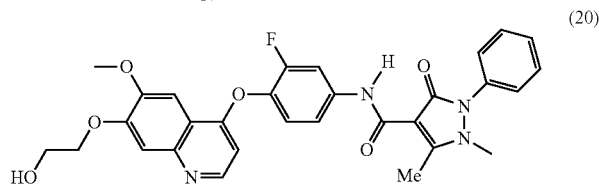
(21)
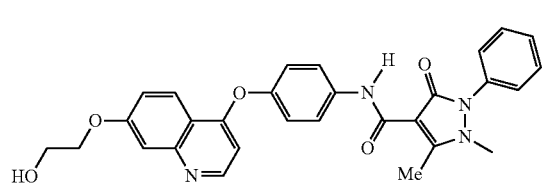
(22)
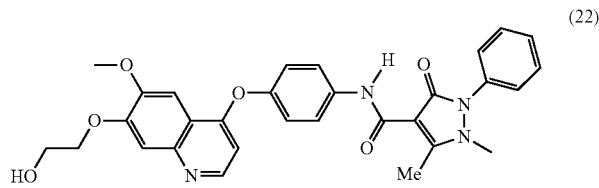
(23)
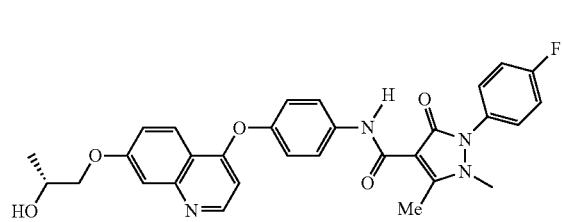
(24)
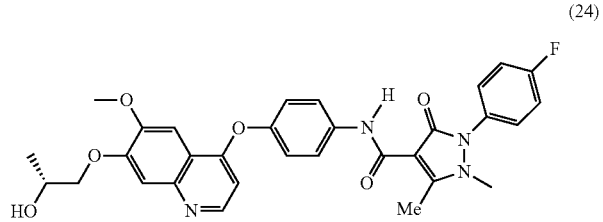
(25)
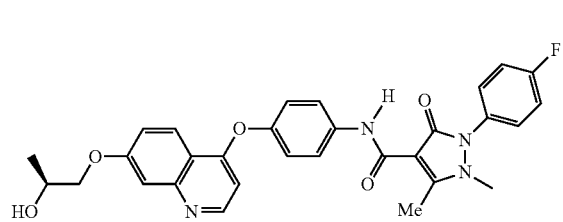
(26)
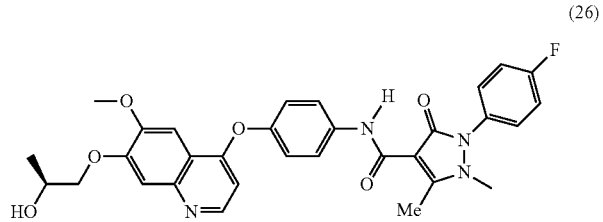
(27)
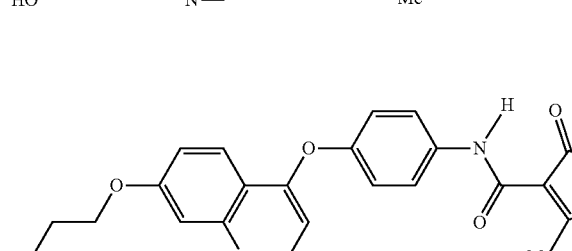
(28)
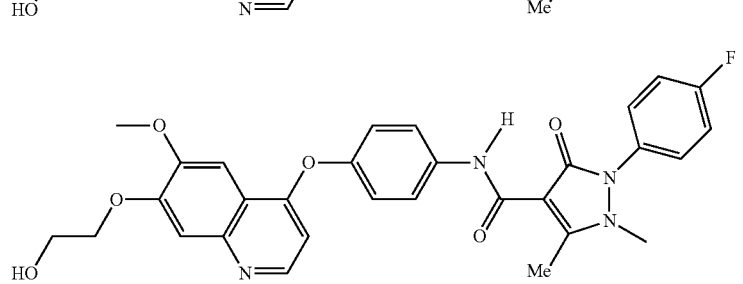

or a stereoisomer, a geometric isomer, a tautomer, an N-oxide, a hydrate, a solvate, a metabolite, a pharmaceutically acceptable salt or a prodrug thereof.

6. A pharmaceutical composition comprising the compound according to claim 1 and a pharmaceutically acceptable carrier, excipient, diluent, adjuvant, vehicle or a combination thereof.

7. The pharmaceutical composition according to claim 6 further comprising a therapeutic agent selected from a chemotherapeutic agent, an anti-proliferative agent, an agent for treating atherosclerosis, an agent for treating lung fibrosis, and combinations thereof.

8. The pharmaceutical composition according to claim 7, wherein the additional therapeutic agent is adriamycin, rapamycin, temsirolimus, everolimus, ixabepilone, gemcitabin, cyclophosphamide, dexamethasone, etoposide, fluorouracil, afatinib, alisertib, amuvatinib, axitinib, bosutinib, brivanib, cabozantinib, cediranib, crenolanib, crizotinib, dabrafenib, dacomitinib, dasatinib, danusertib, dovitinib, erlotinib, foretinib, ganetespib, gefitinib, ibrutinib, imatinib, iniparib, lapatinib, lenvatinib, linifanib, linsitinib, masitinib, momelotinib, motesanib, neratinib, niraparib, nilotinib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, an interferon, carboplatin, topotecan, taxol, vinblastine, vincristine, temozolomide, tositumomab, trabedectin, belimumab, bevacizumab, brentuximab, cetuximab, gemtuzumab, ipilimumab, ofatumumab, panitumumab, ranibizumab, rituximab, tositumomab, trastuzumab or a combination thereof.

\* \* \* \* \*